United States Patent [19]

Shimamura et al.

[11] Patent Number: 5,952,193
[45] Date of Patent: Sep. 14, 1999

[54] PEPTIDE MIXTURE AND PRODUCTS THEREOF

[75] Inventors: Seiichi Shimamura; Yoshitaka Tamura; Hiroshi Miyakawa; Hitoshi Saito; Yasushi Kawaguchi; Naoko Isomura; Yoko Akazome; Hiroshi Ochi; Mihoko Kawamoto, all of Kanagawa, Japan

[73] Assignee: Morinaga Milk Industry Co., Ltd., Tokyo, Japan

[21] Appl. No.: 08/817,095

[22] PCT Filed: Oct. 13, 1995

[86] PCT No.: PCT/JP95/02109

§ 371 Date: Apr. 14, 1997

§ 102(e) Date: Apr. 14, 1997

[87] PCT Pub. No.: WO96/11584

PCT Pub. Date: Apr. 25, 1996

[30] Foreign Application Priority Data

Oct. 14, 1994 [JP] Japan .................................. 6-274303
Oct. 14, 1994 [JP] Japan .................................. 6-274304
Nov. 15, 1994 [JP] Japan .................................. 6-305635

[51] Int. Cl.$^6$ .......................... A23C 21/02; A23C 21/04; A23C 21/06; A61K 38/01
[52] U.S. Cl. ..................... 435/68.1; 426/583; 426/657; 530/343; 530/407; 530/833
[58] Field of Search .................... 530/343, 365, 530/407; 426/41, 42, 583, 657

[56] References Cited

U.S. PATENT DOCUMENTS

| | | | |
|---|---|---|---|
| 4,427,658 | 1/1984 | Maubois et al. | 424/177 |
| 4,981,704 | 1/1991 | Thibault | 426/41 |
| 5,230,902 | 7/1993 | Gold et al. | 424/535 |
| 5,314,873 | 5/1994 | Tomita et al. | 514/21 |
| 5,330,972 | 7/1994 | Cope | 514/2 |
| 5,486,461 | 1/1996 | Nielsen | 435/68.1 |
| 5,780,439 | 7/1998 | Mendy et al. | 514/21 |

*Primary Examiner*—Cecilia J. Tsang
*Assistant Examiner*—Michael Borin
*Attorney, Agent, or Firm*—Oblon, Spivak, McClelland, Maier & Neustadt, P.C.

[57] ABSTRACT

A method for producing a peptide mixture from whey protein by (1) adding at least one protease to an aqueous solution of at least one whey protein to hydrolyze the whey protein, (2) measuring the amount of a free amino acid selected from the group consisting of lysine, phenylalanine, leucine and arginine produced during the hydrolysis of the whey protein, (3) calculating the amount of the free amino acid with respect to the total amount of the amino acid contained in the whey protein, and (4) terminating the hydrolysis when the calculated amount of the free amino acid with respect to the total amount of the amino acid contained in the whey protein falls within a predetermined range. The inventive method provides a whey protein hydrolysate of consistent quality.

13 Claims, 3 Drawing Sheets

PEPTIDE MIXTURE AND PRODUCTS THEREOF

TECHNICAL FIELD

The present invention relates to a whey protein hydrolysate having specific physicochemical properties and a method for producing the same, and in particular to a novel whey protein hydrolysate which has exceptional gastrointestinal absorption properties and amino acid balance, which is effective in preventing and treating food allergies and has antioxidant action, which is palatable, and which can be used in a wide variety of applications, as well as to a method for producing the same.

The present invention also relates to a method in which a peptide mixture containing a specific amount of a free amino acid is produced with consistent quality in a state that is always stable.

The present invention furthermore relates to a method in which a peptide mixture with a low phenylalanine content that can be ingested daily by patients suffering from amino acid metabolic disorder, particularly, phenylketonuria, which is a disease requiring a limited intake of phenylalanine, is produced with consistent quality in a state that is always stable.

In the present specifications, percentages are based on weight, except for transmittance and inhibiting ratios, unless otherwise specified.

BACKGROUND ART

It has recently become clear that, in terms of digestion, oligopeptides have better absorption rates and a better balance of amino acids following absorption than do mixtures of free amino acids (Rakuno Kagaku-Shokuhin no Kenkyu [Dairy Sciences and Food Research], Vol. 39, No. A, p. 283 (1990)). It is also clear that there has been a rapid increase in patients suffering from allergies induced by food proteins, and that many allergies caused by whey protein, particularly β-lactoglobulin, have appeared, particularly in infants (Rakuno Kagaku-Shokuhin no Kenkyu [Dairy Sciences and Food Research], Vol. 39, No. A, p. 283 (1990)). There is a need to reduce the antigenicity of whey protein in food products for infants or to essentially remove whey protein antigen from food products for infants.

The hydrolysis of whey protein has been widely adopted as a means for reducing the antigenicity of whey protein in food products for infants or for essentially removing whey protein antigen from food products for infants, but hydrolysates with an extremely low percentage of free amino acids often taste bad, which can cause problems when they are ingested. Hydrolysates of whey protein are also sometimes unstable against heat, resulting in precipitation in a liquid state, browning, and other such disadvantages which have posed problems when conventional hydrolysates are used as oral nutrients and the like.

Preventing oxidation is another major issue when whey protein hydrolysates are used in food products, particularly in fatty foods (such as powder milk prepared for infants, which contains as much as 27% fat per 100 g). That is, the balance between saturated and unsaturated fatty acids is considered from a nutritional standpoint in food products that contain fats, but a drawback is that unsaturatio d fatty acids are readily oxidized. DHA and the like which are contained in large amounts in the biological membranes of brain, neural, and retinal tissue and which have recently been believed to play a role in the manifestation of their functions release an extremely strong oxidation odor once they are oxidized, having a markedly adverse effect on product quality, and there is thus a need to prevent their further oxidation.

Ingested amino acids are degraded by transglutaminase, glutamate dehydrogenase, and the like to produce ammonia, but the ammonia thus produced is toxic and must be immediately treated by the liver, so it is essential that no ingested foods contain ammonia. In this regard, it is extremely important that whey protein hydrolysates contain no ammonia.

In view of the nitrogen equilibrium in mature animals, nitrogen should be ingested in an amount corresponding to the minimum metabolic amount of nitrogen, but nitrogen is ineffective when just given in the form of ammonia, and it must be ingested in the form of essential amino acids. Foods that are ingested must therefore contain the necessary amounts of essential amino acids.

Many methods for producing hydrolysates by the enzymolysis of whey proteins have been developed in view of the nutritional and physicochemical background of the proteins and amino acids described above. Several examples are given below.

1) Whey protein is hydrolyzed either with two enzymes, one being a *Bacillus subtilis*-derived endopeptidase and one being trypsin, or with three enzymes, including a *Bacillus subtilis*-derived endopeptidase, trypsin, and chymotrypsin, to obtain an oligopeptide mixture with a molecular weight of no more than 2,000 daltons, antigen persistence of no more than $10^{-4}$, and a free acid content of no more than 5% (Japanese Laid-Open Patent Publication 4-248959).

2) Whey protein is hydrolyzed with an alkali protease to obtain a hydrolysate which has at least 75 mol % dipeptides and tripeptides, which has a free amino acid content of less than 5%, which consists of at least four amino acids, and which has less than 20 mol % peptides with an average chain length of 6.2 (Japanese Laid-Open Patent Publication 5-505304).

3) Whey, casein, and soybeans are hydrolyzed with pepsin, trypsin, and chymotrypsin, and ultrafiltration of the product results in an oligopeptide which has a molecular weight of no more than 60,000 daltons and which is 40 to 60% peptides containing 4 to 10 amino acids (Japanese Laid-Open Patent Publication 3-187348).

4) Whey protein is hydrolyzed by thermal denaturation at a pH of 6 to 10 and a temperature of 60 to 80° C., and the enzyme is inactivated by heat to obtain a hydrolysate which has a molecular weight of no more than 10,000 daltons, main peaks of 1,000 to 5,000, an average peptide chain length of 3 to 8, a free amino acid content of no more than 20%, and no more than $\frac{1}{10,000}$ β-lactoglobulin antigenicity (Japanese Laid-Open Patent Publication 4-112753).

5) Whey protein is hydrolyzed with trypsin, α-chymotrypsin, and Aspergillus and Bacillus enzymes to obtain a low allergenic peptide with a molecular weight of no more than 10,000 daltons and the capacity to induce oral immunotolerance (Japanese Laid-Open Patent Publication 5-5000).

6) Casein is hydrolyzed with an acidic protease and is hydrolyzed with a neutral peptidase to obtain a peptide with a molecular weight of no more than 3,000 daltons, a free amino acid content of 30 to 55%, no more than 1 in 10,000 parts $\alpha_s$-casein in an ELISA inhibition test for α$_s$-casein, and a 5% solution bitterness organoleptic value no greater than that corresponding to a 0.04% aqueous solution of caffeine (Japanese Laid-Open Patent Publication 6-113893).

7) A method has been disclosed in which whey is hydrolyzed at a pH of 5 to 11 using a neutral protease (Aspergillus) and then heated at a pH of 2 to 4, and the precipitate is removed to obtain 50% dipeptides and tripeptides (Japanese Patent Publication 5-82412).

Peptide mixtures obtained by the proteolysis of animal proteins (animal milk, eggs, meat, fish, and the like) or vegetable proteins (soybeans, wheat, and the like) are known to have properties such as thickening, foaming, antioxidant, digestive, mineral solubilizing, and low antigenicity properties, as well as epithelial cell growth factor, cell growth factor, calcium absorption promoting function, opioid-like activity, and other such physiologically active functions (Shokuhin to Kaihatsu [Food Products and Development], Vol. 26, No. 11, pp. 28–36 (1991)). They are an indispensable material in the manufacture of meat, fish paste, breads, sweets, mineral fortified food products, infant food products, sports beverages, general health foods, enteric nutrients, food products to combat protein allergies, special nutritional food products, medical drugs, and the like.

Methods for producing the peptide mixtures used in the manufacture of these food products and medical drugs vary, depending on the application, and can be broadly divided into:

a) methods for producing the target peptide mixture by hydrolyzing the starting material protein with only an endopeptidase to minimize the production of free amino acids;

b) methods for hydrolyzing the starting material protein with a combination of an endopeptidase and an exopeptidase to produce a peptide mixture which conversely contains a prescribed amount of free amino acids;

c) methods for purifying and fractionating such peptide mixtures into a target peptide mixture by separation such as ultrafiltration (UV), reverse osmosis (RO), gel filtration, and ion exchange resin methods; and the like.

Phenylketonuria (henceforth PKU) is a congenital metabolic disorder in which phenylalanine (henceforth Phe) accumulates in the blood, resulting in neurological disorders and developmental disorders, due to a congenital deficiency of phenylalanine hydroxylase which converts the amino acid phenylalanine into tyrosine. Patients suffering from PKU must accordingly strictly limit the amounts of Phe ingested under the supervision of a physician so as to avoid the accumulation of Phe in the body.

Since, on the other hand, Phe is a common amino acid that is usually contained in an amount of about 3 to 5% in proteins, patients of PKU have had to ingest part or all of the protein component of food products or infant milk preparations by substituting them with amino acid mixtures containing no Phe. These types of amino acid mixtures, however, suffer from drawbacks such as the disagreeable taste characteristic of amino acids and the diarrhea which results from high osmotic pressure in the intestines. There is thus a desire on the part of patients, their families, and physicians for a palatable source of protein serving as a suitable food therapy for patients of PKU.

A method involving the use of κ-casein glycomacropeptide (henceforth GMP) as a protein source for patients of PKU has been disclosed as one such method (Japanese Laid-Open Patent Publication 4-126051). The amino acid sequence of GMP contains no Phe, the molecular weight is a substantial 8,000 daltons, and the problem of elevated osmotic pressure is virtually absent, making this substance an effective source of protein for patients of PKU. However, the isolation of GMP is extremely complicated and is unsuitable for industrial production. Moreover, recent nutritional findings have made it clear that oligopeptides are more readily digested than proteins.

Another example of the use of oligopeptides as a source of protein for patients of PKU is the method in which proteolysis is brought about with a protease, fractions containing no Phe are recovered by gel filtration, and the resulting low phenylalanine peptide (henceforth LPP) is used (Journal of Food Science, Vol. 41, pp. 1029–1032 (1976), and Japanese Laid-Open Patent Publication 61-68426).

In another method that has been disclosed, proteins are treated with an exopeptidase or are treated with an exopeptidase following treatment with an endopeptidase, activated carbon is used to adsorb polypeptides containing virtually no aromatic amino acids as well as low molecular weight peptides having terminal free aromatic amino acids or aromatic amino acids, and the low molecular weight substances are separated using reverse osmosis membranes or ion exchange electrodialysis membranes to produce LPP (Japanese Patent Publication 2-54070). This method has made the industrial manufacture of LPP possible.

The following conventional techniques are examples for producing peptides by the hydrolysis of starting material proteins using protease.

1) A method that has been disclosed is characterized in that enzymolysis is brought about for 0.5 to 10 hours in an aqueous system containing both an endo-type protease and exo-type protease to obtain oligopeptides with an average chain length of 3 to 10 and with very little bitterness (Japanese Laid-Open Patent Publication 62-143697).

2) In another method that has been disclosed, any starter protein starting material is dispersed to between 5 and 20% (w/v) in water, the pH is adjusted to between 1 and 4 with an acid, and enzymolysis is brought about as two or more acidic proteases are added simultaneously or consecutively to suppress the production of free amino acids for 8 to 72 hours at a temperature of 25 to 60° C., so as to produce a low molecular weight peptide composition (Japanese Patent Publication 57-45560).

3) A method for producing a casein partial hydrolysate by controlling the flow ratio of the casein solution has been disclosed for methods involving the partial hydrolysis of a casein solution using a column packed with an immobilized enzyme (Japanese Patent Publication 3-31421).

4) A method for producing a proteolytic product in which the production of insoluble products is prevented is characterized in that a dissolving promoter and a protein or a substance containing a protein are mixed and dissolved in dissolving water or the like, and one or more proteases is or are added to bring about digestion and thus produce a proteolytic product, during which time the viscosity of the solution obtained following the addition of at least the initial proteolytic product is measured over time, and the digestion reaction is stopped before the viscosity begins to fall following a substantial increase (Japanese Patent Publication 3-58252).

5) A method for inactivating the enzyme by heat treatment when the ratio of hydrolysis reaches 5 to 25% has been disclosed for methods of producing peptide mixtures which are the protease hydrolysates of animal milk κ-casein-derived glycopolypeptide, with a Fisher value ranging from 30 to 60 (Japanese Laid-Open Patent Publication 2-300137).

6) A method for measuring peptide concentration with a peptide sensor and a method for measuring the average chain length of peptides have been disclosed for methods of producing hydrolysates in the hydrolysis of proteins using immobilized proteases (edited by Shokuhin Sangyo Baioriakuta Shisutemu Gijutsu Kenkyu Kumiai [Association for Research on Food Industry Bioreactor Systems], Jissen Baioriakuta [Practical Bioreactors], pp. 166–184, published by Association for Research on Food Industry Bioreactor Systems (1990)).

7) It has been disclosed that gluten hydrolysates with excellent foaming stability can be produced by measuring the hydrophobicity of gluten hydrolysates using reverse phase high performance liquid chromatography (high performance liquid chromatography is henceforth HPLC) in methods for producing gluten hydrolysates by hydrolyzing wheat gluten using immobilized proteases (Jissen Baioriakuta [Practical Bioreactors], pp. 106–126, published by Association for Research on Food Industry Bioreactor Systems (1990)).

8) It is known that the free amino acid content in the target product is measured during processing and management of the fermentation of amino acids such as lysine and glutamic acid and the production of fermented foods such as soy sauce and miso sauce (Shokuhin Kogyo [Food Industry], Vol. 34, No. 16, pp. 1–11 (1991)).

9) A method has been disclosed for producing a low molecular weight peptide with no antigenicity, a molecular weight of no more than 1,000 daltons, a free amino acid content of no more than 20%, and an aromatic amino acid content of no more than 1.0% of the total amino acids by recovering the peptide components through gel filtration following hydrolysis until the starting material protein is no longer found to be antigenic and until the aromatic amino acids contained in the starting material protein are at least 90% free amino acids (Japanese Laid-Open Patent Publication 2-138991).

10) A method that has been disclosed for producing a peptide mixture from cow milk whey protein is characterized in that cow milk whey protein is brought into contact with a protease capable of simulating the digestion of proteins occurring in the body, so as to continue the hydrolysis until the product contains virtually no residual protein, that is, until it contains no nitrogen capable of precipitating in 12% trichloroacetic acid, and until a peptide mixture is obtained in which at least 50% of the peptides contain 2 to 5 amino acids, with a free amino acid content of no more than 15% (Japanese Patent Publication 62-61039).

11) A cosmetic and topical skin agent that has been disclosed is characterized in that the hydrolysate of a protein has a molecular weight of no more than 1,000, with at least 90% of the aromatic amino acids being free amino acids, has action in activating the growth of human skin cells, and has no lactoprotein antigenicity (Japanese Laid-Open Patent Publication 4-26604).

Although decreases in the antigenicity of the whey protein hydrolysate, improvements in the taste, the free amino acid content, the molecular weight distribution, or the like are considered in the aforementioned conventional techniques, no consideration has been given to the ammonia content and the antioxidant action of the whey protein hydrolysate. A drawback in the past has thus been that whey protein hydrolysates could not be used for a wide range of food products.

Moreover, as indicated in the aforementioned conventional techniques, when peptide mixtures are produced by hydrolyzing starting material proteins with proteases, the end point of the hydrolysis reaction has been determined by measuring the hydrolysate viscosity, ratio of hydrolysis, degree of hydrophobicity, or the like using the reaction time, the protein solution flow ratio, and the like as indices, but it is extremely difficult in these methods to achieve an accuratio grasp of the changing physicochemical state of the hydrolysate, particularly the free amino acid content, and a fatal drawback which needs to be remedied in conventional methods for producing peptide mixtures is that each batch which is manufactured results in a peptide mixture with a different free amino acid content and composition, leading to peptide mixtures of inconsistent quality.

Furthermore, to bring about enzyme reaction with good reproducibility, it is necessary to strictly control the reaction temperature, pH, enzyme titer, substratio concentration, and the like, which is impractical for operations on an industrial scale and makes it extremely difficult for practical purposes to obtain a consistent free amino acid ratio.

This means that the production of high quality LPP is also plagued by the following fatal drawbacks. As described above, in LPP manufacturing methods which include a step involving the hydrolysis of proteins using proteases, the method for lowering the Phe content of the peptide mixture is based on the principle that a sufficient amount of Phe is freed from the proteins by the hydrolysis of the proteins using the protease, and that the freed Phe is removed by gel filtration, activated carbon adsorption, or the like, which means the control of the protease-based hydrolysis of the protein is an important technique for producing high quality LPP.

That is, when Phe is insufficiently freed, a low amount of Phe is removed by gel filtration or activated carbon treatment following the enzymolysis, resulting in a peptide mixture with a higher Phe content, which is unsuitable for use by patients suffering from PKU. When too much Phe is freed (in other words, when enzymolysis has progressed too far), there is a higher ratio of free amino acids other than Phe, resulting in extremely poor taste, and other drawbacks include extremely poor therapeutic effects because of the unpleasant taste, the incidence of diarrhea, and the like, so these problems currently need to be resolved. That is, an extremely important issue for producing high quality LPP is to consistently ensure a certain content of free Phe in peptide mixtures obtained by the hydrolysis of proteins using proteases.

DISCLOSURE OF THE INVENTION

The inventors conducted painstaking research in view of the foregoing and perfected the present invention upon discovering a palatable whey protein hydrolysate that is obtained by the hydrolysis of whey protein, that is effective in avoiding, preventing, and treating food allergies, that is readily digested, that has a low ammonia content, that has antioxidant action, and that can be used in a wide range of applications, as well as a method for producing the same.

In view of the above, and as a result of painstaking research on a method for producing a peptide mixture of consistent quality in a state that is always stable in light of the aforementioned conventional techniques, the inventors perfected the present invention upon discovering that the desired peptide mixture is obtained by measuring briefly and over time the amount of a specific amino acid that is freed in the hydrolysate as a result of hydrolysis, by calculating the proportion with the amount of said specific amino acid contained in the starting material protein, and by immediately stopping the hydrolysis when the value falls within a specific range.

Furthermore, in view of the above, and as a result of painstaking research on a method for obtaining a peptide mixture of consistent quality with a low Phe content in a state that is always stable in light of the aforementioned conventional techniques, the inventors perfected the present invention upon discovering that a peptide mixture with a low Phe content is readily obtained by measuring briefly and over time the amount of Phe that is freed in the hydrolysate during the hydrolysis of the proteins using proteases, by calculating the proportion with the total amount of Phe contained in the starting material protein, by immediately stopping the hydrolysis when the value falls within a specific predetermined range, and by removing the freed Phe.

An object of the present invention is to provide a palatable whey protein hydrolysate which has exceptional gastrointestinal absorption properties and amino acid balance, which is effective in preventing and treating food allergies and has antioxidant action, which has a low ammonia content, and which can be used in a wide variety of applications, as well as to a method for producing the same.

Another object of the present invention is to provide a novel method making it possible to readily obtain a peptide mixture that has a consistent free amino acid content and composition, and that is of good quality.

Still another object of the present invention is to over a novel method that makes it possible to readily obtain a peptide mixture that is of good quality, that has a low phenylalanine content, and that can be ingested on a daily basis by patients suffering from PKU in particular.

The first of the inventions resolving the aforementioned drawbacks is a palatable whey protein hydrolysate, characterized in that the hydrolysate of whey protein having a purity of at least 70% (by weight) has the following physicochemical properties a) through h):

a) less than 1% (by weight) of the total hydrolysate consists of fractions having a molecular weight of between 5,000 and 10,000 daltons;

b) the residual antigenic activity is no more than $10^{-5}$, as determined by the ELISA inhibition test using anti-whey protein sera;

c) the amount of free amino acids is 10 to 15% (by weight) with respect to the total amount of amino acids in the hydrolysate;

d) the amount of free lysine is 12 to 20% (by weight) with respect to the total amount of lysine contained in the whey protein;

e) the ammonia content is no more than 0.2% (by weight);

f) the transmittance of a 10% (by weight) solution is at least 98%, as determined at 540 nm using a 1-cm cell;

g) no precipitation results when a 5% (by weight) solution with pH 4 to 7 is heated for 10 minutes at 120° C.; and h) it has antioxidant activity.

The second of the inventions resolving the aforementioned drawbacks is a method for producing a palatable whey protein hydrolysate, characterized in that whey protein with a purity of at least 70% (by weight) is dissolved in water to a concentration of no more than 15% (by weight); the pH of the aqueous solution is adjusted to between 7.5 and 10; two types of proteases, one a *Bacillus subtilis*-derived endopeptidase and the other a lactic acid bacteria-derived exopeptidase, are added to the aqueous solution to initiate hydrolysis; the amount of free lysine in the hydrolysate is measured over time, and the hydrolysis is stopped when the amount of free lysine is between 12 and 20% (by weight) with respect to the total amount of lysine contained in the starting material whey protein; and fractions with a molecular weight of 10,000 daltons or more are completely removed by ultrafiltration.

The third of the inventions resolving the aforementioned drawbacks is a method for producing a peptide mixture of consistent quality, wherein said method for producing a peptide mixture is characterized in that one or more proteases is or are added to an aqueous solution of starting material proteins consisting of one or more proteins or to an aqueous solution of slightly pre-hydrolyzed starting material proteins to start the hydrolysis of the starting material protein or of the slightly pre-hydrolyzed starting material protein, the amount of a specific amino acid freed in the hydrolysate as a result of the hydrolysis is measured briefly and over time, the amount of the specific free amino acid is calculated with respect to the total amount of the specific amino acid contained in the starting material protein or in the slightly pre-hydrolyzed starting material protein, and the hydrolysis is immediately terminated when the calculated value falls within a specific predetermined range. In a preferred embodiment, the specific amino acid is lysine, phenylalanine, leucine, or arginine.

The fourth of the inventions resolving the aforementioned drawbacks is a method for producing a peptide mixture of consistent quality with a low phenylalanine content, wherein said method for producing a peptide mixture with a low phenylalanine content is characterized in that one or more proteases is or are added to an aqueous solution of starting material proteins consisting of one or more proteins or to an aqueous solution of slightly pre-hydrolyzed starting material proteins to start the hydrolysis of the starting material protein or of the slightly pre-hydrolyzed starting material protein, the amount of phenylalanine freed in the hydrolysate as a result of the hydrolysis is measured briefly and over time, the amount of the free phenylalanine is calculated with respect to the total amount of the phenylalanine contained in the starting material protein or in the slightly pre-hydrolyzed starting material protein, the hydrolysis is immediately terminated when the calculated value falls within a specific predetermined range, and the free phenylalanine in the hydrolysate is removed. In a preferred embodiment, the amount of the free phenylalanine is measured using an enzyme membrane sensor.

The present invention is described in detail below, but the description will begin with the second of the present inventions for the sake of simplicity.

The whey protein used as the starting material in the method pertaining to the present invention can be a commercially available product or the like having a purity of at least 70%. Commercially available products with a higher degree of purity, known as whey protein concentratio s (WPC) and whey protein isolates (WPI), are preferred. The whey protein is dissolved in water to a concentration of no more than 15%, and preferably to between 8 and 12%, and the pH is adjusted to between 7.5 and 10, and preferably to between 8 and 9, with an alkaline aqueous solution.

Two proteases, one being a *Bacillus subtilis*-derived endopeptidase and the other being a lactic acid bacteria-derived exopeptidase, are then added to the aforementioned whey protein solution. Other endopeptidases such as trypsin and papain can also be added in extremely low amounts. The addition of exopeptidases other than lactic acid bacteria-derived types should be avoided, however, because of deterioration in the taste.

Commercially available *Bacillus subtilis*-derived endopeptidases can be used, and are added in a proportion of 1,000 to 7,500 PUN units (the units are described below), and preferably 2,000 to 3,000 PUN units, per gram whey protein.

One PUN unit is the enzyme activity resulting in the calorimetric reaction of an allylamino acid corresponding to 1 µg of tyrosine with Folin reagent after 1 minute at 30° C. when a *Bacillus subtili*-derived endopeptidase is allowed to act on casein (Hammerstein: by Merck).

A lactic acid bacteria-derived exopeptidase can be manufactured as follows by the method noted in the section entitled "(3) Enzymes Used" in Japanese Patent Publication 54-36235, column 6, line 4, for example.

A lactic acid bacteria (including Bifidobacterium) is cultured by a known method (such as the method noted in Japanese Patent Publication 48-43878), the resulting broth is centrifuged to recover the lactic acid bacteria cells, the cells are suspended in sterilized water, and the lactic acid bacteria cells are recovered by centrifugation. This is repeated twice, and the cells are washed, suspended at a concentration of 20% in sterilized water, ruptured with a cell rupturing device (for example, the KDL model dyne-o-mill by Willy Bachnfen Engineering Works), and lyophilized to obtain a lactic acid bacteria-derived exopeptidase powder.

The enzyme is added in a proportion of 20 to 200 active units (the units are described below), and preferably 60 to 90 active units.

An active unit is determined by the following method. Powder containing exopeptidase is dispersed or dissolved in a proportion of 0.2 g/100 mL in 0.1 mol phosphate buffer (pH 7.0) to prepare an enzyme solution. Leucyl para-nitroanilide (by Kokusan Kagaku; henceforth Leu-pNA) is meanwhile dissolved in 0.1 mol phosphate buffer (pH 7.0) to prepare a 2 mM substrate solution. 1 mL substrate solution is added to 1 mL enzyme solution, a reaction is brought about for 5 minutes at 37° C., and the reaction is then stopped with the addition of 2 mL of 30% acetic acid solution. The reaction solution is filtered with a membrane filter, and the filtrate absorbance is determined at a wavelength of 410 nm. One active unit of exopeptidase is defined as the amount of enzyme needed to degrade 1 (mol of Leu-pNA in 1 minute, as determined by the following formula.

Active unit(per gram powder)=20×($A/B$)

A and B in the above formula indicate the absorbance of the sample and the absorbance of 0.25 mM para-nitroaniline, respectively, at a wavelength of 410 nm.

The solution to which the enzyme has been added is maintained at 30 to 60° C., and preferably 45 to 55° C. to initiate the hydrolysis of the whey protein. When the pH falls as the hydrolysis progresses, the pH should be kept at 6 or more, and preferably between 6 and 7.

After the hydrolysis has been initiated, the amount of free lysine in the hydrolysate is measured over time using a device capable of measuring the amount of free lysine in the hydrolysate over time, such as a Biotech Analyzer (by Asahi Kasei Kogyo), and when the proportion of free lysine is within 12 to 20%, and preferably 14 to 17%, with respect to the total amount of lysine contained in the starting material whey protein, the reaction liquid is immediately heated (for example, 15 minutes at 85° C.) to inactivate the enzyme and stop the hydrolysis.

The resulting reaction solution is adjusted to a pH of between 5.5 and 7 with an acid such as citric acid and is subjected to ultrafiltration using a well-known device (such as the Ultrafiltration Module by Asahi Kasei Kogyo), so as to completely remove fractions with a molecular weight of 10,000 daltons or more and obtain the targeted, palatable whey protein hydrolysate. The liquid containing the whey protein hydrolysate can be concentratio d by a well-known method to produce a concentrated liquid, and the concentratio d liquid can also be dried by a well-known method to make a powder.

The whey protein hydrolysate obtained in the manner described above has the following physicochemical properties, as will be elucidated in the practical examples below.

a) As indicated in FIG. 1, less than 1% (by weight) of the total hydrolysate consists of fractions having a molecular weight of between 5,000 and 10,000 daltons. It contains no fractions with a molecular weight of 10,000 daltons or more. At least 70% of the fractions have a molecular weight of less than 1,000 daltons. It has peaks at a molecular weight of 500 daltons and a molecular weight of 1,000 daltons. The number average molecular weight is 300 to 400 daltons, and the weight average molecular weight is 600 to 800 daltons.

FIG. 1 indicates the molecular weight distribution of the whey protein hydrolysate of the present invention obtained in Example 1. The vertical and horizontal axes indicate the distribution ratio and the molecular weight, respectively.

b) As shown in FIG. 2, the residual antigenic activity is no more than $10^{-5}$, and preferably no more than $10^{-6}$, as determined by the ELISA inhibition test using anti-whey protein sera.

FIG. 2 indicates the residual antigenic activity of the whey protein hydrolysate of the present invention obtained in Example 1. The vertical and horizontal axes indicate the inhibiting ratio and final sample concentration, respectively. In the figure, plus signs and boxes indicate the whey protein hydrolysate of the present invention and whey protein, respectively.

c) The amount of free amino acids is 10 to 15% (by weight), and preferably 11 to 13% (by weight), with respect to the total amount of amino acids in the hydrolysate.

d) The amount of free lysine is 12 to 20% (by weight), and preferably 14 to 17% (by weight), with respect to the total amount of lysine contained in the whey protein.

e) The ammonia content is no more than 0.2% (by weight), and preferably no more than 0.1% (by weight).

f) The transmittance of a 10% (by weight) solution is at least 98%, as determined at 540 nm using a 1-cm cell.

g) No precipitation results when a 5% (by weight) solution with pH 4 to 7 is heated for 10 minutes at 120° C.

h) As shown in FIG. 3, it has antioxidant activity equal to or greater than that of α-tocopherol, a well-known antioxidant. FIG. 3 indicates the antioxidant activity of the whey protein hydrolysate of the present invention obtained in Example 1. The vertical and horizontal axes indicate the residual antioxidant capacity and the time, respectively. In the figure, the diamonds, plus signs, and boxes indicate the whey protein hydrolysate of the present invention, α-tocopherol, and a control (sample or preparation added), respectively.

The third of the inventions is described below.

The starting proteins used as starting material in the method pertaining to the present invention are not particularly limited and include animal proteins (such as those derived from animal milk, eggs, fish, meat, and the like), vegetable proteins (such as those derived from grains, seaweed, rice, and the like), and any mixture of these. Peptide mixtures of substantial molecular weight which are hydrolysates of slightly pre-hydrolyzed proteins and which can be further hydrolyzed proteases can be used as starting material.

The starting material aqueous solution is prepared by dissolving the starting protein or slightly pre-hydrolyzed starting protein in water to a concentration of around 10%, calculated in terms of protein, and by adjusting the solution pH with an alkali solution or acid solution to around the optimal pH of the protease being used.

Animal-derived (such as pancreatin, pepsin, trypsin, and the like), vegetable-derived (such as papain, bromelain, and the like), microbe-derived (such as mold, actinomyces, bacteria, lactic acid bacteria, or the like) proteases, or any combination of these, may be selected as desired according to the intended use and added in the prescribed amounts. In a preferred embodiment, for example, the endopeptidase can be added in an amount of 2000 to 5000 PUN units per gram starting protein, and the exopeptidase can be added in an amount of 20 to 100 active units per gram starting protein.

The starting material aqueous solution to which the prescribed amounts of enzymes have been added is usually maintained for a prescribed time at the optimal temperature of the enzymes to bring about the zymolysis of the protein. When microbial growth is a concern during the hydrolysis, the solution can be maintained as needed for a prescribed time at a temperature higher or lower than the optimal temperature of the enzymes to bring about the zymolysis of the protein.

The hydrolysis is initiated, and the amount of a specific amino acid in the hydrolysate is measured briefly and over time. Specifically, this can be done using, for example, an HPLC, a Biotech Analyzer (by Asahi Kasei Kogyo), a perfusion chromatograph (BioCAD by Perceptive Biosystems), and the like. Because the amount of amino acid that is freed varies, depending on the type of starting protein and enzyme used, amino acids that are freed in large amounts should be selected as the specific amino acid. In a particularly preferable embodiment, the amount of specific amino acid freed in the hydrolysate can be measured on-line. Examples of specific amino acids that are particularly preferred include lysine, phenylalanine, leucine, and arginine. In this way, the amount of the specific amino acid freed in the hydrolysate is measured briefly and over time, and when the proportion of the specific free amino acid falls within a specific predetermined range with respect to the total amount of the specific amino acid contained in the starting material protein, the enzymes in the reaction solution are immediately inactivated or removed to stop the hydrolysis. The aforementioned specific range varies, depending on the target peptide mixture, the starting material that is used, the enzymes that are used, and the like, but when, for example, the whey protein is hydrolyzed as the amount of free lysine is measured briefly and over time, a range of 5 to 40% can be given as an example of the range for the amount of free lysine.

The method for inactivating or removing the enzymes in the reaction liquid to stop the hydrolysis is not particularly limited in the present invention, and a desired method may be used, although there are cases where there are time lags until the hydrolysis is stopped (for example, it sometimes takes 30 to 60 minutes to heat a certain amount of hydrolysate until the enzyme is inactivated). In such cases, because of the risk of continuing hydrolysis, pre-tests should be conducted in advance, the ratioat which the hydrolysis progresses (for example, the velocity at which the specific free amino acid is produced) should be measured based on prescribed conditions, and the time needed to inactivate or remove the enzyme should be taken into account to determine and establish the aforementioned specific range.

The hydrolysate containing the completely hydrolyzed peptide mixture can be concentrated by a common method to make a concentrated liquid, and the concentratio d liquid can be dried by a common method to make a powder. The liquid containing the peptide mixture can also be purified by a common method such as ultrafiltration and gel filtration and concentratio d by a common method to make a concentratio d liquid, and the concentrated liquid can be dried by a common method to make a powder.

The configuration of the reaction vessel in which the hydrolysis is carried out (such as tanks, tubes, columns, or the like), the mode of hydrolysis (such as batch, continuous, or consecutive modes), the method for inactivating, separating, or removing the enzymes, the method for purifying the peptides, and the like are not particularly limited, and common methods and devices can be used.

A peptide mixture of consistent quality, in which the free amino acid content and composition are always constant, can be manufactured in the manner described above.

The fourth of the inventions is described below.

The starting protein used as starting material in the present invention is not particularly limited and may be an animal protein derived from animal milk, eggs, fish, meat or the like, vegetable proteins derived from soybeans, wheat, or the like, or any mixture of these. Peptide mixtures of substantial molecular weight which are hydrolysates of slightly pre-hydrolyzed proteins and which can be further hydrolyzed by proteases can be used as starting material.

The starting protein or slightly pre-hydrolyzed starting protein is dissolved in water to a concentration of around 10%, calculated in terms of protein, and a 5 to 30 minute heat treatment at a temperature ranging between 65 and 90° C. may be undertaken to ensure efficient sterilization and zymolysis of the proteins. The solution pH is then adjusted with an alkali solution or acid solution to around the optimal pH of the protease being used so as to prepare the starting material aqueous solution.

The protease is then added to the aforementioned starting material aqueous solution. The protease may be added all at once or consecutively by being added a little at a time. Examples of proteases which are used include animal-derived (such as pancreatin, pepsin, trypsin, chymotrypsin, and the like), vegetable-derived (such as papain, bromelin, and the like), and microbe-derived (such as yeast, mold, bacteria, actinomyces, lactic acid bacteria, or the like) endoproteases and exoproteases. Those having affinity for aromatic amino acids such as Phe are preferred as endoproteases. Examples include pepsin, chymotrypsin, and the like. Those showing peptidase activity for peptides that have an aromatic amino acid such as Phe at the terminal are preferred as exoproteases. Desirable examples which can be used include exopeptidases derived from Aspergillus, Actinomyces, yeast, and the like.

To ensure that enough Phe is freed, the aforementioned endoprotease and exoprotease should be used in combination. The hydrolysis can be brought about by adding the enzymes all at once to the starting protein solution, or in steps by adding the endoprotease, and then adding the exoprotease after a certain time has elapsed. In a preferred embodiment, for example, the enzymes are added in amounts such that the endopeptidase is added in an amount of 5000 to 10000 PUN units per gram starting protein, and the exopeptidase is added in an amount of 10 to 50 active units per gram starting protein.

The starting material aqueous solution to which the prescribed amounts of enzymes have been added is usually maintained for a prescribed time at the optimal temperature of the enzymes to bring about the zymolysis of the protein. When microbial growth is a concern during the hydrolysis, the solution can be maintained as needed for a prescribed time at a temperature higher or lower than the optimal temperature of the enzymes to bring about the zymolysis of the protein. However, the temperature should usually range from 40 to 60° C. because the hydrolysis efficiency decreases in a temperature range that differs significantly from the optimal temperature of the enzymes.

After the hydrolysis is initiated, the amount of a Phe freed in the hydrolysate is measured briefly and over time. This can be done using, for example, an HPLC, an enzyme membrane sensor (such as a Biotech Analyzer (by Asahi Kasei Kogyo)), and the like. In a particularly preferable embodiment, a method of on-line measurement can be used. In this way, the amount of Phe freed in the hydrolysate is measured briefly and over time, and when the proportion of the free Phe falls within a specific predetermined range with respect to the total amount of the Phe contained in the starting material protein or slightly pre-hydrolyzed protein, the enzymes in the hydrolysate are immediately inactivated or removed to stop the hydrolysis. Because the Phe contained in the starting protein or slightly pre-hydrolyzed protein must be freed and removed at high levels to provide a peptide mixture for patients suffering from PKU, the aforementioned specific range can be 85 to 95%, and preferably 88 to 92%.

The enzymes can be inactivated or removed from the hydrolysate using common heat treatments, ultrafiltration, or the like. Temperature and time conditions which allow the enzymes to be sufficiently inactivated in the heat treatment can be established as desired in view of the thermal stability of the enzymes that are used. When a certain time is needed to inactivate or remove the enzymes by heat treatment or ultrafiltration, during which there is a chance that the hydrolysis will continue, the ratioat which the hydrolysis progresses (for example, the velocity at which the Phe is freed) should be tested in advance based on certain conditions, and the aforementioned specific range in which the hydrolysis is to be stopped should be determined and established on the basis of the results.

After the enzymes in the hydrolysate have been inactivated or removed, the hydrolysate is cooled by a common method, and the precipitate is removed from the hydrolysate by a method such as celite filtration, precision filtration, ultrafiltration, or centrifugation. The aromatic amino acids such as Phe can be removed from the resulting hydrolysate by a desired method such as gel filtration, an adsorptive resin method, an activated carbon adsorption method, or the like, either alone or in combination. A gel filtration agent with a molecular weight cut-off of 10,000 daltons or less, and preferably 2,500 daltons or less, is used, and the use of a gel carrier having aromatic amino acid-adsorbing hydrophobic side chains, such as carboxyl groups, butyl groups, phenyl groups, and hydrophobic sites, is particularly preferred. Examples of such gel filtration agents include Sephadex G-10 (by Pharmacia) and Cellulofine GCL-25 (by Seikagaku Kogyo), and examples of activated carbon include Sirasagi (by Takeda Yakuhinn Kogyo).

A column is packed with the gel filtration agent or activated carbon, and the hydrolysate is allowed to flow through the column. Water can be used as the eluate, or a 2 to 15% ethanol aqueous solution can be used to enhance the aromatic amino acid adsorption. The aromatic amino acids can be removed by a batch method in which the gel filtrate agent or activated carbon is placed in the hydrolysate and allowed to stand for a prescribed time so as to adsorb the aromatic amino acids.

The solution of the peptide mixture with a low phenylalanine content obtained by the aforementioned method can then be concentratio d by a common method to make a concentratio d liquid, and the concentrated liquid can be dried by a common method to make a powder. The solution, concentratio d liquid, or powder of the peptide mixture with a low phenylalanine content thus obtained can be used as starting material for food products designed for patients suffering from PKU in the same way as ordinary food product starting materials so as to manufacture a variety of food products for patients suffering from PKU.

Figure 1:
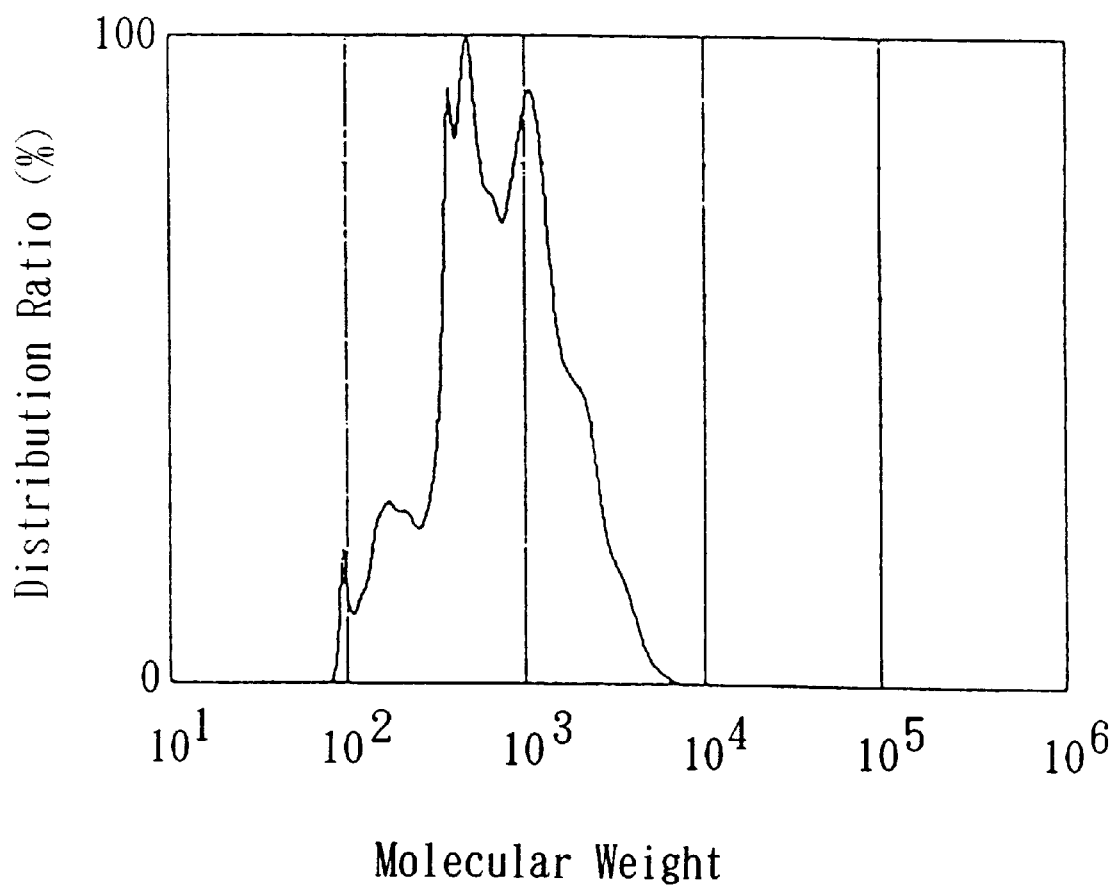
FIG. 1 shows the molecular weight distribution of the whey protein hydrolysate pertaining to the present invention.

Test examples are given below to describe the present invention. The following test methods were employed in the test examples of the present invention.

(1) Method for Determining Molecular Weight

Molecular weight was determined by HPLC as described below (Nobuo Ui et al, editors, "Tanpakushitsu-Pepuchido no Kosokuekitai Kuromatogurafi [High Performance Liquid Chromatography of Proteins and Peptides]", Special Issue of Kagaku [Chemistry], No. 102, p. 241, Kagaku Dojin (1984)). Polyhydroxyethyl-Asparamide columns (by PolyLC; diameter of 4.6 mm, and length of 200 mm) were used to elute samples with 20 mM sodium chloride and 50 mM formic acid at an elution ratio of 0.4 mL/min. Samples were detected with a UV detector, and data was analyzed with a GPC analysis system (by Shimadzu Seisakusho).

(2) Method for Assaying Residual Antigen Activity

Residual antigen activity was assayed by the ELISA inhibition test (Nihon Shoni Arerugi Gakkaishi [Journal of the Japan Pediatric Allergy Society], Vol. 1, p. 36 (1978)) as described below. 96-well plates (by Nunc) were coated with whey protein and washed, a mixture of rabbit anti-whey protein serum and hydrolysate sample was introduced into the plate wells and allowed to react, the plates were washed and then allowed to react with alkali phosphatase-labeled goat anti-rabbit IgG antibodies (by Zymed Laboratory), the plates were washed and p-nitrophenyl-sodium phosphate was added, 5 N sodium hydroxide was added after 30 minutes to stop the reaction, and the reaction product was measured with a microplate reader (by Wako Junyaku Kogyo).

The inhibiting ratio was calculated by the following formula to express the extent to which the reaction was inhibited by the addition of the subject antigen solution for suppression.

Inhibiting ratio(%)=(1−absorbance of subject antigen solution/absorbance of control)×100

The values for the subject antigen solution absorbance and the control absorbance were obtained following reaction in wells in which an equivalent amount of subject sample solution or a mixture of a diluent had been introduced, respectively, to anti-whey protein serum.

(3) Method for Determining Amino Acid Composition

Amino acids other than tryptophan, cysteine, and methionine were analyzed with an amino acid analyzer (by Hitachi Seisakusho; model 835) by hydrolyzing samples for 24 hours at 110° C. in 6 N hydrochloric acid, while tryptophan was analyzed by (alkali) dissolving samples for 22 hours at 110° C. in barium hydroxide, and cysteine and methionine were analyzed by hydrolyzing samples for 18 hours at 110° C. in 6 N hydrochloric acid following treatment with performic acid, so as to measure amino acid mass.

(4) Method for Determining Free Amino Acid Composition

Free amino acid mass was determined by the deproteinization of samples with sulfosalicylic acid for analysis with an amino acid analyzer (by Hitachi Seisakusho; model 835). The percentage of free amino acid mass with respect to the amino acid mass values obtained in the previous analysis of amino acid composition was then calculated.

(5) Method for Determining Free Lysine Content

A lysine-measuring enzyme electrode, a 20 mM L-lysine reference solution, 0.1 M phosphate L-lysine measuring buffer, and a detergent surfactant (all by Asahi Kasei Kogyo) were used to measure the free lysine concentration with a Biotech Analyzer (by Asahi Kasei Kogyo) both in batches and on-line, and the proportion of the amount of free lysine with respect to total lysine was calculated based on the free lysine content of the hydrolysate with respect to the lysine content of the protein.

(6) Method for Measuring Ammonia Content

The ammonia mass was measured by the deproteinization of samples with sulfosalicylic acid for analysis with an amino acid analyzer (by Hitachi Seisakusho; model 835).

(7) Method for Determining Antioxidant Action

Linoleic acid and β-carotene were emulsified with Tween 20, a sample or α-tocopherol as a preparation was added therein, and the changes over time were measured by colorimetry (Phytochemistry, Vol. 10, p. 1445 (1971)). The final concentrations of linoleic acid, β-carotene, Tween 20, sample, and α-tocopherol were 0.96 mg/mL, 4.8 µg/mL, 9.6 mg/mL, 0.19 mg/mL, and 0.19 mg/mL, respectively.

(8) Method for Determining Free Lysine Content

A lysine-measuring enzyme electrode, a 20 mM L-lysine reference solution, 0.1 M phosphate L-lysine measuring buffer, and a detergent surfactant (all by Asahi Kasei Kogyo) were used to measure the free lysine concentration with a Biotech Analyzer (by Asahi Kasei Kogyo) both in batches and on-line, and the proportion of the amount of free lysine with respect to total lysine was calculated based on the free lysine content of the hydrolysate with respect to the lysine content of the starting protein.

(9) Method for Determining Free Phe Content

The free amino acid content was measured using a Biotech Analyzer (by Asahi Kasei Kogyo) equipped with a free amino acid concentration-measuring enzyme electrode (by Asahi Kasei Kogyo), and the free Phe content in the hydrolysate was determined based on the correlation of values between the resulting value and a predetermined free Phe ratiotested beforehand.

(10) HPLC

An Inertsil PREP-ODS (by GL Science; 6.5×250 mm) column was mounted on an HPLC (by Shimadzu Seisakusho), and 0.1 mL hydrolysate was eluted at a flow ratioof 1.5 mL/min with a concentration gradient such that the proportion of eluant B (0.1% trifluoroacetic acid-acetonitrile solution) with respect to eluant A (0.1% trifluoroacetic acid solution) reached 50% in 100 minutes.

(11) Ratio of Hydrolysis

The total nitrogen of a sample was measured by the Kjeldahl method, the formol state nitrogen of a sample was measured by formol titration, and the ratio of hydrolysis was calculated by the following formula.

Ratio of hydrolysis(%)=(formol state nitrogen)/(total nitrogen)× 100

The ratio of hydrolysis (%) is the percentage of the formol state nitrogen content of the hydrolysate per total nitrogen content of the starting material protein solution. It is, specifically, calculated by the following method. 4 mL protein solution and 30 mL distilled water are mixed, and the pH is adjusted to 6.8 with 0.2 N sodium hydroxide solution or hydrochloric acid solution. This solution is titrated with 0.1 N sodium hydroxide solution until the pH reaches 7.9 following the addition of 5 mL of a formalin solution adjusted to pH 8.0 with 0.2 N sodium hydroxide solution. The ratio of hydrolysis is calculated using the following formula, where A mL is the amount titratio d at this time, F is the 0.1 N sodium hydroxide solution factor, and B (%) is the protein concentration of the starting material protein solution.

Ratio of hydrolysis(%)=22.3×A×F/B

Test 1

This test was conducted to check the optimal concentration of the whey protein solution subjected to hydrolysis using as an index the percentage of high molecular weight fractions closely related to antigenicity.

1) Preparation of Samples

Whey protein solutions were hydrolyzed by the same method as in Example 1 except that the whey protein concentration was changed as shown in Table 1 to prepare seven samples.

2) Test Method

The percentage of fractions having a molecular weight of 5,000 to 10,000 daltons was determined by the aforementioned method for determining molecular weight.

3) Test Results

The test results are given in Table 1. As may be seen in Table 1, it was determined that a whey protein concentration of no more than 15%, and preferably no more than 12%, resulted in less than 1% fractions having a molecular weight of 5,000 to 10,000 daltons. A range of 8 to 12% was ideal from the standpoint of reaction efficiency. Virtually the same results were obtained when tests were conducted by changing the type of whey protein, the type of *Bacillus subtilis*-derived endopeptidase and lactic acid bacteria-derived exopeptidase, and the amounts of the enzymes within the range determined in Test 3 described below.

TABLE 1

| Whey protein concentration (%) | Fractions (%) with a molecular weight of 5,000 to 10,000 daltons |
|---|---|
| 5 | 0.2 |
| 8 | 0.3 |
| 10 | 0.3 |
| 12 | 0.3 |
| 15 | 0.9 |
| 18 | 1.5 |
| 20 | gelled |

Test 2

This test was conducted to check the optimal range for initial pH in the enzyme treatment for hydrolysis using antigenicity as an index.

1) Preparation of Samples

Whey protein solutions were hydrolyzed in the same manner as in Example 1 except that the initial pH during hydrolysis was changed as follows to prepare five samples.

Sample 1: hydrolyzed after initial pH adjusted to 6.5
Sample 2: hydrolyzed after initial pH adjusted to 7.5
Sample 3: hydrolyzed after initial pH adjusted to 8.0
Sample 4: hydrolyzed after initial pH adjusted to 9.0
Sample 5: hydrolyzed after initial pH adjusted to 10.0

2) Test Method

The residual antigenic activity was assayed by the aforementioned method for assaying residual antigenic activity.

3) Test Results

The test results are given in Table 2. As may be seen in Table 2, it was determined that an initial pH of 7.5 to 10.0, and particularly 8 to 9, was desirable during hydrolysis for obtaining whey protein hydrolysates with low antigenicity. Virtually the same results were obtained when tests were conducted by changing the type of whey protein, the type of *Bacillus subtilis*-derived endopeptidase and lactic acid bacteria-derived exopeptidase, and the amounts of the enzymes within the range determined in Test 3 described below.

TABLE 2

| Sample No. | Initial pH in Enzyme Treatment | Residual Antigenic Activity |
| --- | --- | --- |
| 1 | 6.5 | $10^{-5}$ |
| 2 | 7.5 | $10^{-6}$ |
| 3 | 8.0 | $<10^{-6}$ |
| 4 | 9.0 | $<10^{-6}$ |
| 5 | 10.0 | $10^{-6}$ |

Test 3

This test was conducted to check the optimal amount of enzymes to be used. The percentage of high molecular weight fractions closely related to antigenicity, the ammonia content, and the antioxidant activity were used as indices.

1) Preparation of Samples

Whey protein solutions were hydrolyzed in the same manner as in Example 1 except that the amounts of enzyme used were changed as shown in Table 3 to prepare twelve samples. The free lysine content in Sample Nos. 1 and 7 had not reached 14% even after 30 hours of hydrolysis, so hydrolysis was terminated at that point in time.

2) Test Method

The percentage of fractions having a molecular weight of 5,000 to 10,000 daltons was determined by the aforementioned method for determining molecular weight, the ammonia content was measured by the aforementioned method for measuring ammonia content, and the antioxidant activity was assayed by the aforementioned method for assaying antioxidant activity. The antioxidant activity of the samples was expressed using as an index the strength relative to the antioxidant activity of α-tocopherol.

3) Test Results

The test results are given in Table 3. As may be seen in Table 3, it was determined that no more than 1% consisted of fractions with a molecular weight of 5,000 to 10,000 daltons, that the ammonia content was no more than 0.2%, and that the antioxidant activity was equal to or better than that of α-tocopherol when the enzymes were used in the following amounts: *Bacillus subtilis*-derived endopeptidase in an amount of 1,000 to 7,500 PUN units, and preferably 2,000 to 3,000 PUN units, and lactic acid bacteria-derived exopeptidase in an amount of 20 to 200 active units, and preferably 60 to 90 active units, per gram whey protein. Virtually the same results were obtained when tests were conducted by changing the types of whey protein, *Bacillus subtilis*-derived endopeptidase, and lactic acid bacteria-derived exopeptidase.

TABLE 3

| | Amount of enzyme added (per gram substrate) | | Fractions (%) with molecular | | |
| --- | --- | --- | --- | --- | --- |
| Sample No. | Enzyme 1 (PUN unit) | Enzyme 2 (active unit) | weight of 5,000 to 10,000 daltons | Ammonia content (%) | Antioxidant activity |
| 1 | 0 | 90 | 64 | 0.03 | + |
| 2 | 1000 | 90 | 0.9 | 0.05 | ++ |
| 3 | 2000 | 90 | 0.3 | 0.09 | ++ |
| 4 | 3000 | 90 | 0.2 | 0.11 | ++ |
| 5 | 7500 | 90 | 0.3 | 0.10 | ++ |
| 6 | 10000 | 90 | 0.3 | 0.14 | + |
| 7 | 3000 | 0 | 1.4 | 0.03 | |
| 8 | 3000 | 20 | 1.0 | 0.05 | ++ |
| 9 | 3000 | 60 | 0.3 | 0.05 | ++ |
| 10 | 3000 | 90 | 0.2 | 0.11 | ++ |
| 11 | 3000 | 200 | 0.2 | 0.18 | ++ |
| 12 | 3000 | 300 | 0.2 | 0.33 | + |

(Note 1) Enzymes 1 and 2 were Protease N Amano (*Bacillus subtilis*-derived endopeptidase) and the product of ruptured *Lactobacillus helveticus* cells (lactic acid bacteria-derived exopeptidase), respectively.
(Note 2) Key to symbols for antioxidant activity
+: indicates less antioxidant activity than α-tocopherol
++: indicates antioxidant activity equal to or greater than that of α-tocopherol Test 4

This test was conducted to check the optimal ratio at which lysine is freed in hydrolysate using as indices flavor, the percentage of high molecular weight fractions closely related to antigenicity, and the free amino acid content affecting flavor.

1) Preparation of Samples

Seven samples were prepared by the same method as in Example 1 except that the hydrolysis reaction was stopped by inactivating the enzymes at the desired proportion of the free lysine content, as shown in Table 4.

2) Test Method

The percentage of fractions having a molecular weight of 5,000 to 10,000 daltons and the content of free amino acids were determined by the aforementioned methods. The flavor was tested by the following method.

a) Flavor Test

Flavor was evaluated in an organoleptic test by a panel of ten each of males and females. Flavor was evaluated based on four ranks from good (0 point) to poor (3 points). An average of less than 0.5 was ratio d as good, 0.5 to less than 1.5 as fair, 1.5 to less than 2.5 as somewhat poor, and 2.5 to less than 3.0 as poor.

3) Test Results

The test results are given in Table 4. As may be seen in Table 4, it was determined that whey protein hydrolysate with good flavor was obtained when the ratio at which lysine was freed was between 12 and 20%, and preferably between 14 and 17%. Virtually the same results were obtained when tests were conducted by changing the type of whey protein, the type of *Bacillus subtilis*-derived endopeptidase and lactic acid bacteria-derived exopeptidase, and the amounts of the enzymes within the range determined in Test 3 above.

TABLE 4

| Free lysine content (%) | Flavor | Fractions (%) with molecular weight of 5,000 to 10,000 daltons | Free amino acids (%) |
| --- | --- | --- | --- |
| 0.1 | poor | 21 | 0.2 |
| 6 | somewhat poor | 1.5 | 5 |
| 12 | fair | 0.4 | 10 |
| 14 | good | 0.3 | 11 |
| 17 | good | 0.2 | 13 |

TABLE 4-continued

| Free lysine content (%) | Flavor | Fractions (%) with molecular weight of 5,000 to 10,000 daltons | Free amino acids (%) |
| --- | --- | --- | --- |
| 20 | fair | 0.2 | 15 |
| 27 | somewhat poor | 0.2 | 20 |

Test 5

This test was conducted to check the optimal filtration method for the hydrolysate, using as indices the percentage of high molecular weight fractions closely related to antigenicity, antigenicity, transmittance as the basis of the transparency serving as an ideal property of food materials, and thermal stability.

1) Preparation of Samples

Whey protein solutions were hydrolyzed by the same method as in Example 1 except that the filtration membranes (fraction molecular weight) were changed as shown in Table 5 to prepare three samples. A microfiltration membrane with a pore diameter of 0.25 (m and 3,000 dalton and 10,000 dalton molecular weight fraction ultrafiltration membranes by Asahi Kasei Kogyo were used as filtration membranes.

2) Test Method

The percentage of fractions with a molecular weight of 5,000 to 10,000 daltons, the residual antigenic activity, the transmittance, and the thermal stability were determined by the aforementioned methods.

3) Test Results

The results of the test are given in Table 5. As may be seen in Table 5, it was determined that ultrafiltration affording less than 1% fractions with a molecular weight of 5,000 to 10,000 daltons, a transmittance of at least 98% and thermal stability required the use of a 10,000 molecular weight fraction or less, and preferably a 3,000 molecular weight fraction or less, ultrafiltration membrane, with a pH adjusted to between 5.5 and 7 using citric acid. Virtually the same results were obtained when tests were conducted by changing the type of whey protein, the type of *Bacillus subtilis*-derived endopeptidase and lactic acid bacteria-derived exopeptidase, and the amounts of the enzymes within the range determined in Test 3 above.

TABLE 5

| Molecular weight | pH | Fractions (%) with mol. wt. 5,000 to 10,000 daltons | Residual antigenic activity | Transmittance (%) | Thermal stability | |
| --- | --- | --- | --- | --- | --- | --- |
| | | | | | pH 5.5 to 7 | pH 4 |
| 3000 daltons | 7.0 | 0.2 | $<10^{-6}$ | 99 | – | – |
| 10000 daltons | 5.5 | 0.3 | $<10^{-6}$ | 98 | – | – |
| 0.25 μm microfiltration membrane | 6.5 | 1.5 | $10^{-4.5}$ | 96 | + | + |

(Note)
Negative and positive signs indicate no precipitation and precipitation, respectively.

Test 6

This test was conducted to check the optimal type of enzyme for hydrolysis using flavor and antioxidant activity as indices.

1) Six samples were prepared by the same method as in Example 1 except that the types and amounts of enzymes used were changed as shown in Table 6. Bioplase 6.OS (Nagase Seikagaku Kogyo) was used as the *Bacillus subtilis*-derived endopeptidase, and the products of ruptured *Lactobacillus helveticus* cells or of *Bifidobacterium breve* cells prepared by the same method as in Reference Example 1 below were used as the lactic acid bacteria-derived exopeptidase, while trypsin (by Novo Nordisk) was used as another endopeptidase, and Denatyme AP (by Nagase Sangyo) was used as another exopeptidase. Since the free lysine content had not reached 14% even after 30 hours of hydrolysis in Sample Nos. 1 and 2, the hydrolysis was terminated at that point in time.

2) Test Method

The flavor and antioxidant activity were determined by the aforementioned methods.

3) Test Results

The test results are given in Table 6. As may be seen in Table 6, it was determined that palatable whey protein hydrolysates with antioxidant activity equal to or greater than that of α-tocopherol were obtained by hydrolysis with two types of proteases, one being a *Bacillus subtilis*-derived endopeptidase and the other being a lactic acid bacteria-derived exopeptidase. Virtually the same results were obtained when tests were conducted by changing the type of whey protein and the amount and type of enzyme (by changing the amounts of *Bacillus subtilis*-derived endopeptidase and lactic acid bacteria-derived exopeptidase within the range determined in Test 3 above).

TABLE 6

| Sample No. | Enzyme used and amount added (per gram substrate) | | Flavor | Antioxidant activity |
| --- | --- | --- | --- | --- |
| 1 | Bioplase | 3000 PUN units | poor | ++ |
| 2 | Lactobacillus helveticus | 90 active units | poor | + |
| 3 | Bioplase Bifidobacterium breve | 3000 PUN units 90 active units | good | ++ |
| 4 | Bioplase Lactobacillus helveticus | 3000 PUN units 90 active units | good | ++ |
| 5 | Trypsin Lactobacillus helveticus | 3000 PUN units 90 active units | somewhat poor | + |
| 6 | Bioplase Denatyme AP | 3000 PUN units 90 active units | somewhat poor | ++ |

(Note) Key to symbols for antioxidant activity
+: indicates less antioxidant activity than α-tocopherol
++: indicates antioxidant activity equal to or greater than that of α-tocopherol

REFERENCE EXAMPLE 1

100 parts (by weight; same below) tap water and 5 parts lime were added to 20 parts corn steep liquor, the acid contained in the corn steep liquor was neutralized, and the product was filtered with the addition of 50 partslcelite as a filtration agent to obtain filtratio A. Separately from this, a mixture of 20 parts fish liver, 35 parts molasses, and 200 parts tap water was filtered with the addition of 50 parts celite to obtain filtratio B.

5 parts glucose, 2.5 parts monopotassium phosphate, 2.5 parts dipotassium phosphate, and 5 parts sodium acetate were added to 500 parts of an equivalent mixture of the aforementioned filtrates A and B, the pH was adjusted to 6.4 with 30% sodium hydroxide, and the total amount was brought to 1000 parts by adding water.

*Lactobacillus helveticus* was cultured in 10 L of sterilized medium having the aforementioned composition, the resulting broth was centrifuged to recover the Lactobacillus cells, and the cells were suspended in sterilized water and centrifuged to recover the Lactobacillus cells. This was repeated twice, the cells were washed and then suspended in sterilized water to a concentration of 20%, and the cells were ruptured using an ultrasonic rupturing device (Sonifier model 250 by Bronson) and lyophilized to obtain approximately 25 g of lactic acid bacteria-derived exopeptidase powder.

REFERENCE EXAMPLE 2

25.0 kg whey protein hydrolysate obtained by the same method as in Example 2 (protein equivalent of 79.4%) was dissolved in 140 kg water, the prescribed amount of minerals dissolved in 5 kg water was added, the solution was heated to 60° C., 2.0 kg vegetable fat containing 70 g DHA, 65.1 kg malt dextrin, 6.6 kg sugar, and the prescribed amounts of vitamins were mixed, and this mixture was thoroughly homogenized with a high pressure homogenizer, sterilized for 2 seconds at 120° C. and spray dried to obtain about 99 kg of an anti-allergenic composition in the form of a powder.

Test 7

This test was a comparative study of the effects on the quality (changes in free amino acid composition and free amino acid content) of peptide mixtures manufactured by conventionally used peptide mixture manufacturing methods, that is 1) a method in which the zymolysis was stopped based on reaction time, 2) a method in which the zymolysis was stopped based on ratio of hydrolysis, and 3) the method of the present invention.

1) Preparation of Samples

A total of 15 samples were prepared by repeating five times the hydrolysis of whey protein solutions by the same method as in Example 8 except that the zymolysis was stopped at 4 hours in method 1) above, the zymolysis was stopped when the ratio of hydrolysis reached 23% in method 2) above, and the zymolysis was stopped when the ratio at which lysine was freed reached 15% as the concentration of free lysine in the hydrolysate was measured over time and briefly in 3) the method of the present invention.

2) Test Method

The free amino acid content and free amino acid composition of the samples were determined by the aforementioned methods, and the average value (Mean) and standard deviation (S.D.) were determined from five sets of results.

3) Test Results

The test results are given in Table 7. It may be seen in Table 7 that, despite some differences in the average values (Mean) for the content of each free amino acid and the total free amino acid content in the peptide mixtures manufactured in the methods above, the standard deviation values (S.D.) for the content of each free amino acid and the total content of free amino acids were lowest and most stable in 3) the method of the present invention, followed by low level changes in method 2), with method 1) showing the greatest changes and the most unstable manufacturing quality.

TABLE 7

| Amino acid | Free amino acid content (g/100 g) in method 1) | | Free amino acid content (g/100 g) in method 2) | | Free amino acid content (g/100 g) in method 3) | |
|---|---|---|---|---|---|---|
| | Mean | S.D. | Mean | S.D. | Mean | S.D. |
| L-aspartic acid | 0.15 | 0.042 | 0.16 | 0.031 | 0.16 | 0.021 |
| L-threonine | 0.50 | 0.061 | 0.55 | 0.044 | 0.54 | 0.030 |
| L-serine | 0.57 | 0.060 | 0.59 | 0.044 | 0.57 | 0.029 |
| L-glutamic acid | 0.36 | 0.043 | 0.32 | 0.032 | 0.32 | 0.021 |
| L-glycine | 0.18 | 0.042 | 0.16 | 0.031 | 0.13 | 0.020 |
| L-alanine | 0.61 | 0.061 | 0.65 | 0.047 | 0.64 | 0.032 |
| L-valine | 0.71 | 0.063 | 0.70 | 0.049 | 0.68 | 0.034 |
| L-cystine | 0 | 0 | 0 | 0 | 0 | 0 |
| L-methionine | 0.72 | 0.075 | 0.75 | 0.048 | 0.75 | 0.037 |
| L-isoleucine | 0.30 | 0.043 | 0.31 | 0.032 | 0.33 | 0.022 |
| L-leucine | 2.85 | 0.108 | 2.95 | 0.078 | 2.92 | 0.054 |
| L-tyrosine | 0.42 | 0.041 | 0.43 | 0.034 | 0.40 | 0.023 |
| L-phenylalanine | 0.63 | 0.062 | 0.68 | 0.049 | 0.68 | 0.033 |
| L-tryptophan | 0.44 | 0.054 | 0.49 | 0.040 | 0.46 | 0.027 |
| L-lysine | 1.22 | 0.101 | 1.27 | 0.071 | 1.25 | 0.046 |
| L-histidine | 0.29 | 0.042 | 0.31 | 0.032 | 0.28 | 0.021 |
| L-arginine | 1.14 | 0.085 | 1.15 | 0.067 | 1.10 | 0.042 |
| L-proline | 0.09 | 0.035 | 0.10 | 0.030 | 0.11 | 0.019 |
| Total free amino acid content | 11.18 | 0.555 | 11.57 | 0.428 | 11.32 | 0.202 |

Test 8

This test was conducted to compare the methods when hydrolysis was carried out under different conditions of hydrolysis using different starting material proteins than those in Test 7.

1) Preparation of Samples and Test Method 15 samples were prepared by repeating hydrolysis five times by the same method as in Test 7 except that 1 kg bovine milk casein (tradename: ALACID, 90% protein content, by New Zealand Dairy Board) was suspended as the protein starting material in 9 kg deionized water, the pH was adjusted to 7.0 with 20% caustic soda solution, and the material was dissolved; the zymolysis was stopped at 9 hours in method 1) above; the zymolysis was stopped when the ratio of hydrolysis reached 30% in method 2) above; and the zymolysis was stopped when the ratio at which lysine was freed reached 32% as the concentration of free lysine in the hydrolysate was measured over time and briefly in 3) the method of the present invention.

2) Test Results

The test results are given in Table 8. It may be seen in Table 8 that, despite some differences in the average values (Mean) for the content of each free amino acid and the total free amino acid content in the peptide mixtures manufactured in the methods above, the standard deviation values (S.D.) for the content of each free amino acid and the total content of free amino acids were lowest and most stable in 3) the method of the present invention, followed by method 2), with method 1) showing the greatest changes and the most unstable manufacturing quality.

TABLE 8

| Amino acid | Free amino acid content (g/100 g) in method 1) | | Free amino acid content (g/100 g) in method 2) | | Free amino acid content (g/100 g) in method 3) | |
|---|---|---|---|---|---|---|
| | Mean | S.D. | Mean | S.D. | Mean | S.D. |
| L-aspartic acid | 0.22 | 0.048 | 0.26 | 0.022 | 0.24 | 0.021 |
| L-threonine | 0.60 | 0.061 | 0.64 | 0.043 | 0.64 | 0.033 |
| L-serine | 0.93 | 0.079 | 0.95 | 0.052 | 0.94 | 0.037 |
| L-glutamic acid | 0.57 | 0.061 | 0.60 | 0.044 | 0.57 | 0.029 |
| L-glycine | 0.20 | 0.041 | 0.21 | 0.031 | 0.21 | 0.019 |
| L-alanine | 0.41 | 0.053 | 0.42 | 0.038 | 0.41 | 0.025 |
| L-valine | 0.95 | 0.068 | 0.97 | 0.050 | 0.98 | 0.037 |
| L-cystine | 0 | 0 | 0 | 0 | 0 | 0 |
| L-methionine | 1.00 | 0.089 | 1.09 | 0.069 | 1.05 | 0.044 |
| L-isoleucine | 1.02 | 0.088 | 1.00 | 0.073 | 1.02 | 0.041 |
| L-leucine | 3.53 | 0.131 | 3.68 | 0.099 | 3.61 | 0.066 |
| L-tyrosine | 0.85 | 0.069 | 0.89 | 0.051 | 0.89 | 0.034 |
| L-phenylalanine | 1.72 | 0.106 | 1.81 | 0.076 | 1.76 | 0.051 |
| L-tryptophan | 0.31 | 0.041 | 0.36 | 0.033 | 0.35 | 0.022 |
| L-lysine | 2.40 | 0.121 | 2.42 | 0.084 | 2.42 | 0.058 |
| L-histidine | 0.71 | 0.062 | 0.73 | 0.047 | 0.71 | 0.032 |
| L-arginine | 1.88 | 0.111 | 1.95 | 0.081 | 1.91 | 0.055 |
| L-proline | 0.17 | 0.046 | 0.20 | 0.031 | 0.21 | 0.020 |
| Total free amino acid content | 17.47 | 0.751 | 18.18 | 0.511 | 17.92 | 0.355 |

Test 9

This test was conducted to compare the methods when hydrolysis was carried out under different conditions of hydrolysis using different starting material proteins than those in Tests 7 and 8.

1) Preparation of Samples and Test Method 15 samples were prepared by repeating hydrolysis five times by the same method as in Test 7 except that the protein starting material was changed to soybean protein (tradename: SUPRO; 90% protein content, by Fuji Seiyu); the zymolysis was stopped at 6 hours in method 1) above; the zymolysis was stopped when the ratioof hydrolysis reached 13% in method 2) above; and the zymolysis was stopped when the ratioat which lysine was freed reached 21% as the concentration of free lysine in the hydrolysate was measured over time and briefly in 3) the method of the present invention.

2) Test Results

The test results are given in Table 9. It may be seen in Table 9 that, despite some differences in the average values (Mean) for the content of each free amino acid and the total free amino acid content in the peptide mixtures manufactured in the methods above, the standard deviation values (S.D.) for the content of each free amino acid and the total content of free amino acids were lowest and most stable in 3) the method of the present invention, followed by method 2), with method 1) showing the greatest changes and the most unstable manufacturing quality.

Tests were similarly conducted with the protein starting material changed to meat, fish, eggs, and the like, but it was determined in all cases that the changes in the free amino acid composition and the free amino acid content were lowest and most stable in the method of the present invention.

Test 10

This test was conducted to check methods for measuring specific free amino acids.

1) Preparation of Samples and Test Methods

Peptide mixtures were prepared from whey protein by the same method as in method 3) in Test 7 above except that the free lysine content in the hydrolysate was measured briefly and over time using an HPLC (by Shimadzu Seisakusho) instead of the Biotech Analyzer (by Asahi Kasei Kogyo).

2) Test Results

The test results are given in Table 10. It may be seen in Table 10 that, despite some differences in the average values (Mean) for the content of each free amino acid and the total free amino acid content when the amount of free lysine in the hydrolysate was measured with a Biotech Analyzer and when measured with an HPLC, there were no substantial differences in the standard deviation values (S.D.) for the content of each free amino acid and the total content of free amino acids between the two methods. It was thus determined that either measuring method could be used in the present invention to measure the free amino acid content. Tests were conducted with different types of protein under different conditions of hydrolysis, but virtually the same results were obtained.

TABLE 10

| Amino acid | Free amino acid content (g/100 g) measured with Biotech Analyzer | | Free amino acid content (g/100 g) measured with HFLC | |
| --- | --- | --- | --- | --- |
| | Mean | S. D. | Mean | S. D. |
| L-aspartic acid | 0.16 | 0.021 | 0.18 | 0.020 |
| L-threonine | 0.54 | 0.030 | 0.51 | 0.031 |
| L-serine | 0.57 | 0.029 | 0.59 | 0.027 |
| L-glutamic acid | 0.32 | 0.021 | 0.33 | 0.022 |

TABLE 9

| Amino acid | Free amino acid content (g/100 g) in method 1) | | Free amino acid content (g/100 g) in method 2) | | Free amino acid content (g/100 g) in method 3) | |
| --- | --- | --- | --- | --- | --- | --- |
| | Mean | S.D. | Mean | S.D. | Mean | S.D. |
| L-aspartic acid | 0.15 | 0.033 | 0.14 | 0.029 | 0.10 | 0.018 |
| L-threonine | 0.27 | 0.035 | 0.20 | 0.033 | 0.22 | 0.019 |
| L-serine | 0.94 | 0.101 | 0.91 | 0.079 | 0.94 | 0.053 |
| L-glutamic acid | 0.22 | 0.035 | 0.18 | 0.026 | 0.18 | 0.015 |
| L-glycine | 0.43 | 0.042 | 0.42 | 0.033 | 0.43 | 0.023 |
| L-alanine | 0.93 | 0.075 | 0.87 | 0.051 | 0.89 | 0.035 |
| L-valine | 0.37 | 0.043 | 0.36 | 0.033 | 0.35 | 0.022 |
| L-cystine | 0 | 0 | 0 | 0 | 0 | 0 |
| L-methionine | 0.90 | 0.078 | 0.88 | 0.052 | 0.91 | 0.037 |
| L-isoleucine | 0.52 | 0.054 | 0.51 | 0.037 | 0.52 | 0.025 |
| L-leucine | 1.09 | 0.089 | 1.01 | 0.063 | 1.06 | 0.043 |
| L-tyrosine | 0.87 | 0.071 | 0.85 | 0.055 | 0.85 | 0.037 |
| L-phenylalanine | 0.91 | 0.073 | 0.89 | 0.056 | 0.88 | 0.036 |
| L-tryptophan | 0.17 | 0.039 | 0.08 | 0.029 | 0.11 | 0.016 |
| L-lysine | 1.13 | 0.077 | 1.11 | 0.061 | 1.13 | 0.043 |
| L-histidine | 0.35 | 0.043 | 0.28 | 0.031 | 0.31 | 0.021 |
| L-arginine | 2.32 | 0.131 | 2.24 | 0.099 | 2.22 | 0.059 |
| L-proline | 0.18 | 0.035 | 0.10 | 0.027 | 0.08 | 0.015 |
| Total free amino acid content | 11.75 | 0.539 | 11.03 | 0.417 | 11.18 | 0.200 |

TABLE 10-continued

| Amino acid | Free amino acid content (g/100 g) measured with Biotech Analyzer | | Free amino acid content (g/100 g) measured with HFLC | |
|---|---|---|---|---|
| | Mean | S. D. | Mean | S. D. |
| L-glycine | 0.13 | 0.020 | 0.15 | 0.021 |
| L-alanine | 0.64 | 0.032 | 0.65 | 0.033 |
| L-valine | 0.68 | 0.034 | 0.68 | 0.031 |
| L-cystine | 0 | 0 | 0 | 0 |
| L-methionine | 0.75 | 0.037 | 0.77 | 0.037 |
| L-isoleucine | 0.33 | 0.022 | 0.31 | 0.023 |
| L-leucine | 2.92 | 0.054 | 2.88 | 0.051 |
| L-tyrosine | 0.40 | 0.023 | 0.42 | 0.019 |
| L-phenylalanine | 0.68 | 0.033 | 0.72 | 0.031 |
| L-tryptophan | 0.46 | 0.027 | 0.44 | 0.024 |
| L-lysine | 1.25 | 0.046 | 1.25 | 0.045 |
| L-histidine | 0.28 | 0.021 | 0.29 | 0.021 |
| L-arginine | 1.10 | 0.042 | 1.15 | 0.047 |
| L-proline | 0.11 | 0.019 | 0.13 | 0.021 |
| Total free amino acid content | 11.32 | 0.202 | 11.45 | 0.212 |

Test 11

This test was conducted to investigate the types of specific free amino acids measured.

1) Preparation of Samples and Test Method

Peptide mixtures were prepared from casein by the same method as in method 3) in Test 8 except that the zymolysis was stopped when the free phenylalanine content reached 25% as the free phenylalanine content in the hydrolysate was measured briefly and over time using an HPLC (by Shimadzu Seisakusho).

2) Test Results

The test results are given in Table 11. It may be seen in Table 11 that there were low standard deviation values (S.D.) for the content of each free amino acid and the total content of free amino acids when the content of free phenylalanine in the hydrolysate was measured, and that a peptide mixture of consistent quality was obtained from the casein. Tests were conducted with different types of protein under different conditions of hydrolysis, but virtually the same results were obtained.

TABLE 11

| Amino acid | Free amino acid content (g/100 g) | |
|---|---|---|
| | Mean | S. D. |
| L-aspartic acid | 0.12 | 0.018 |
| L-threonine | 0.36 | 0.022 |
| L-serine | 0.54 | 0.025 |
| L-glutamic acid | 0.36 | 0.020 |
| L-glycine | 0.13 | 0.017 |
| L-alanine | 0.25 | 0.019 |
| L-valine | 0.63 | 0.033 |
| L-cystine | 0 | 0 |
| L-methionine | 0.68 | 0.037 |
| L-isoleucine | 0.61 | 0.033 |
| L-leucine | 2.14 | 0.057 |
| L-tyrosine | 0.58 | 0.024 |
| L-phenylalanine | 1.04 | 0.041 |
| L-tryptophan | 0.18 | 0.017 |
| L-lysine | 1.37 | 0.047 |
| L-histidine | 0.39 | 0.021 |

TABLE 11-continued

| Amino acid | Free amino acid content (g/100 g) | |
|---|---|---|
| | Mean | S. D. |
| L-arginine | 1.21 | 0.044 |
| L-proline | 0.10 | 0.016 |
| Total free amino acid content | 10.69 | 0.213 |

Test 12

This test was conducted by changing the type of specific free amino acid measured in the same manner as in Test 11 above.

1) Preparation of Samples and Test Method

Peptide mixtures were prepared from soybean protein by the same method as in method 3) in Test 9 except that the zymolysis was stopped when the free leucine content reached 10% as the free leucine content in the hydrolysate was measured briefly and over time using an HPLC (by Shimadzu Seisakusho).

2) Test Results

The test results are given in Table 12. It may be seen in Table 12 that there were low standard deviation values (S.D.) for the content of each free amino acid and the total content of free amino acids when the content of free leucine in the hydrolysate was measured, and that a peptide mixture of consistent quality was obtained from the soybean protein. Virtually the same results were obtained when the free arginine content was measured. Tests were conducted with amino acids other than the aforementioned leucine and arginine and with different types of protein under different conditions of hydrolysis, but virtually the same results were obtained.

TABLE 12

| Amino acid | Free amino acid content (g/100 g) | |
|---|---|---|
| | Mean | S. D. |
| L-aspartic acid | 0.10 | 0.019 |
| L-threonine | 0.15 | 0.021 |
| L-serine | 0.63 | 0.033 |
| L-glutamic acid | 0.13 | 0.020 |
| L-glycine | 0.28 | 0.022 |
| L-alanine | 0.63 | 0.035 |
| L-valine | 0.22 | 0.021 |
| L-cystine | 0 | 0 |
| L-methionine | 0.65 | 0.034 |
| L-isoleucine | 0.35 | 0.021 |
| L-leucine | 0.72 | 0.035 |
| L-tyrosine | 0.58 | 0.028 |
| L-phenylalanine | 0.61 | 0.031 |
| L-tryptophan | 0.10 | 0.018 |
| L-lysine | 0.81 | 0.036 |
| L-histidine | 0.21 | 0.017 |
| L-arginine | 1.22 | 0.045 |
| L-proline | 0.08 | 0.015 |
| Total free amino acid content | 7.47 | 0.187 |

REFERENCE EXAMPLE 3

100 parts (by weight; same below) tap water and 5 parts lime were added to 20 parts corn steep liquor, the acid contained in the corn steep liquor was neutralized, and the product was filtered with the addition of 50 parts celite as a filtration agent to obtain filtratio A. Separately from this, a mixture of 20 parts fish liver, 35 parts molasses, and 200 parts tap water was filtered with the addition of 50 parts celite to obtain filtratio B.

5 parts glucose, 2.5 parts monopotassium phosphate, 2.5 parts dipotassium phosphate, and 5 parts sodium acetate were added to 500 parts of an equivalent mixture of the aforementioned filtrates A and B, the pH was adjusted to 6.4 with 30% sodium hydroxide, and the total amount was brought to 1000 parts by adding water.

*Lactobacillus helveticus* was cultured in 10 L of sterilized medium having the aforementioned composition, the resulting broth was centrifuged to recover the Lactobacillus cells, and the cells were suspended in sterilized water and centrifuged to recover the Lactobacillus cells. This was repeated twice, the cells were washed and then suspended in sterilized water to a concentration of 20%, and the cells were ruptured using an ultrasonic rupturing device (Sonifier model 250 by Bronson) and lyophilized to obtain approximately 25 g of lactic acid bacteria-derived exopeptidase powder.

Test 13

In this test, peptide mixtures were produced by conventionally used methods for manufacturing peptide mixtures, that is, 4) a method in which the zymolysis was stopped based on the reaction time, 5) a method in which the zymolysis was stopped based on the ratio of hydrolysis, and 6) the method of the present invention (enzyme membrane sensor (Biotech Analyzer, by Asahi Kasei Kogyo)), so as to compare the effects on the amount of free Phe in the resulting peptide mixtures and on the Phe content of peptide mixtures with a low Phe content obtained by removing the free Phe from said peptide mixtures.

1) Preparation of Samples

A total of 15 samples were prepared by repeating five times the hydrolysis of bovine milk whey protein solutions by the same method as in Example 12 except that the zymolysis was stopped at 15 hours in method 4) above, the zymolysis was stopped when the ratio of hydrolysis reached 30% in method 5) above, and the zymolysis was stopped when the ratio at which Phe was freed reached 90% as the concentration of free Phe in the hydrolysate was measured over time and briefly in 6) the method of the present invention. Samples were also prepared by removing the free Phe by the same method as in Example 12 from the hydrolysates obtained by these three methods.

2) Test method

The free Phe content in the hydrolysates and the total Phe content in each sample were determined by the aforementioned methods, and the average value (Mean) and standard deviation (S.D.) were determined from five sets of results.

3) Test Results

The test results are given in Table 13. It may be seen in Table 13 that the standard deviation values (S.D.) for the content of free Phe in the sample obtained by the above methods were lowest in 6) the method of the present invention, and that the quality was consistent even when manufactured five times. This was followed by low level changes in method 5), with method 4) showing the greatest changes and the most unstable quality. The values for total Phe in the samples prepared by these three methods and the standard deviation values were also lowest and the quality was most consistent in 6) the method of the present invention. Tests were also conducted with different types of enzymes and different types of starting material protein, but virtually the same results were obtained.

TABLE 13

| Specimen | Method 4) | | Method 5) | | Method 6) | |
| --- | --- | --- | --- | --- | --- | --- |
| | Mean | S.D. | Mean | S.D. | Mean | S.D. |
| Free Phe in hydrolysate | 2.4 | 0.095 | 2.6 | 0.078 | 2.6 | 0.053 |
| Total Phe in samples | 0.3 | 0.095 | 0.3 | 0.058 | 0.2 | 0.033 |

(Note)
Numerical values are number of grams per 100 grams

Test 14

This test was conducted to compare methods when hydrolysis was brought about with different starting material proteins under different conditions of hydrolysis than those in Test 13.

1) Preparation of Samples

A total of 15 hydrolysates were prepared when bovine milk casein was hydrolyzed five times by the same method as in Example 13 except that the zymolysis was stopped at 20 hours in method 4) in Test 13 above, the zymolysis was stopped when the ratioof hydrolysis reached 35% in method 5) in Test 13 above, and zymolysis was stopped when the ratio at which Phe was freed reached 90% as the concentration of free Phe in the hydrolysate was measured briefly and over time in 6) the method of the present invention in Test 13 above. Samples were also prepared by removing the free Phe by the same method as in Example 13 from the hydrolysates obtained by these three methods.

2) Test Method

This was based on the same method as in Test 13.

3) Test Results

The test results are given in Table 14. It may be seen in Table 14 that the standard deviation values (S.D.) for the content of free Phe in the hydrolysates obtained by the above methods were lowest in 6) the method of the present invention, and that the quality was consistent even when manufactured five times. This was followed by low level changes in method 5), with method 4) showing the greatest changes and the most unstable quality. The values for total Phe in the samples prepared by these three methods and the standard deviation values (S.D.) were also lowest and the quality was most consistent in 6) the method of the present invention.

Tests were also conducted with different types of enzymes and different types of starting material protein, but virtually the same results were obtained.

TABLE 14

| Specimen | Method 4) | | Method 5) | | Method 6) | |
| --- | --- | --- | --- | --- | --- | --- |
| | Mean | S.D. | Mean | S.D. | Mean | S.D. |
| Free Phe in hydrolysate | 3.6 | 0.135 | 3.5 | 0.087 | 3.65 | 0.061 |
| Total Phe in samples | 0.4 | 0.112 | 0.3 | 0.062 | 0.3 | 0.035 |

(Note)
Numerical values are number of grams per 100 grams

BEST MODE FOR CARRYING OUT THE INVENTION

The present invention is described in greater detail below with reference to practical examples, but the present invention is not limited to the following practical examples.

EXAMPLE 1

1 kg of whey protein powder with a purity of 75% (by California Protein) was dissolved in 9 kg of deionized water, the solution was sterilized for 15 seconds at 75° C., the pH was adjusted to 9.0, 1,800,000 PUN units (2400 PUN units per gram whey protein) of Protease N Amano (by Amano Seiyaku) and 68,000 active units (90 active units per gram whey protein) of the product of ruptured *Lactobacillus helveticus* cells prepared by the same method as in Reference Example 1 above were added, the solution was hydrolyzed while kept at 50° C., the content of free lysine was measured over time using a Biotech Analyzer (by Asahi Kasei Kogyo), the enzymes were inactivated by 6 minutes of heating at 80° C. when the free lysine content reached 14%, the product was cooled, the pH was then adjusted to 6.0 with citric acid, and the product was subjected to ultrafiltration with a 10,000 molecular weight fraction ultrafiltration membrane (by Nitto Denko) to obtain about 16 kg of a solution containing 5.9% whey protein hydrolysate.

Figure 2:
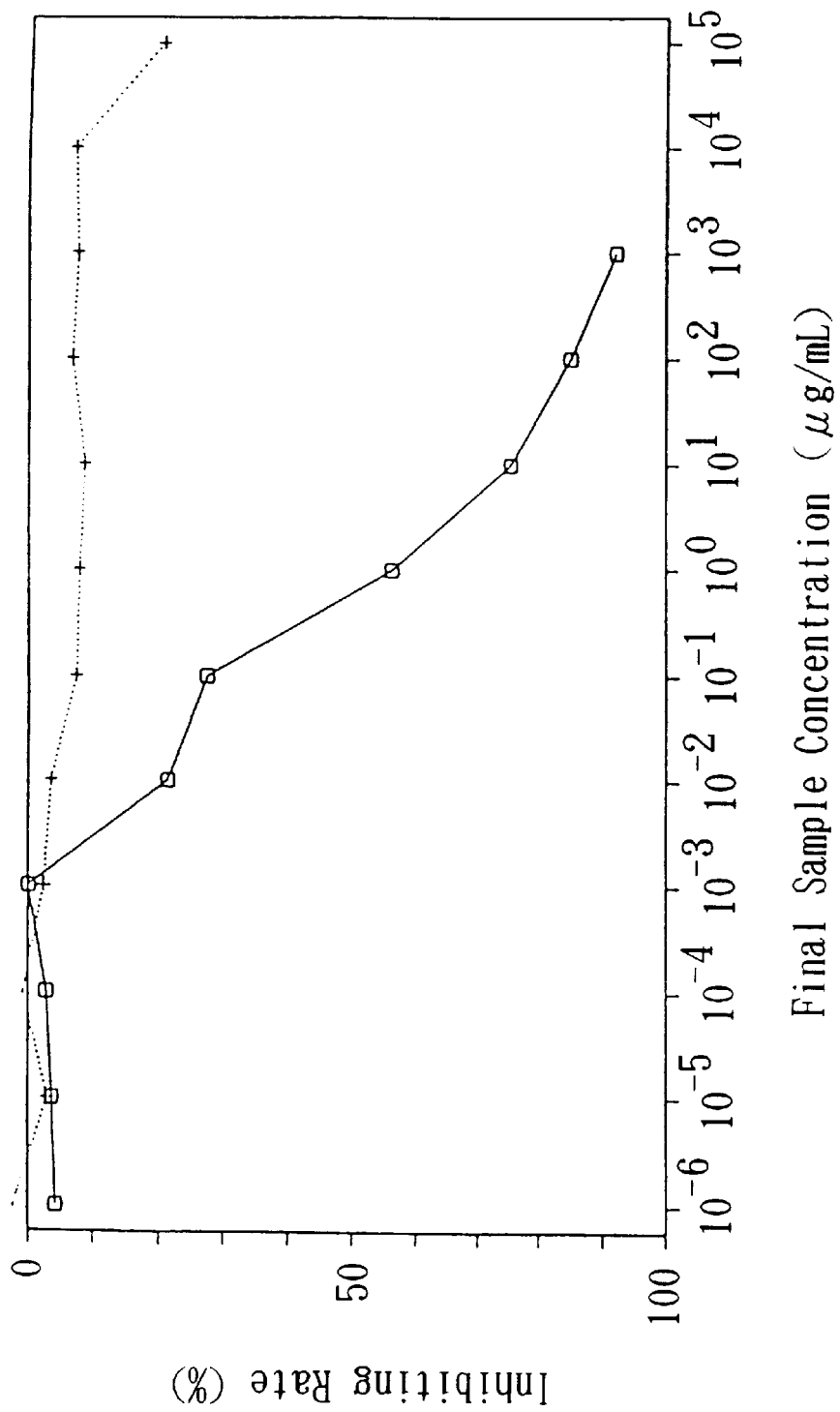
FIG. 2 shows the antigen persistence of the whey protein hydrolysate pertaining to the present invention.
Figure 3:
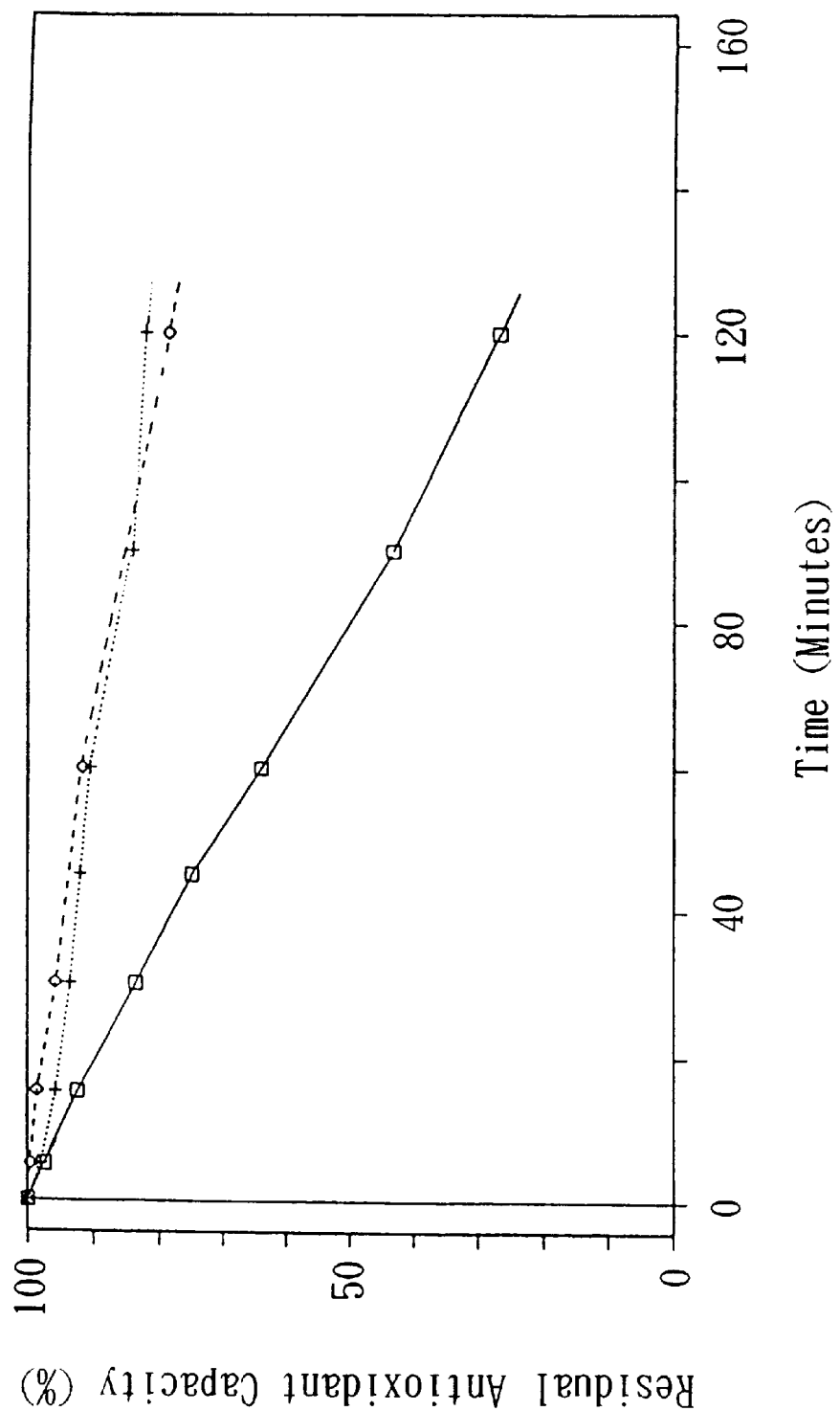
FIG. 3 shows the antioxidant activity of the whey protein hydrolysate pertaining to the present invention.

FIGS. 1, 2, and 3 show some of the results obtained when the resulting whey protein hydrolysate was tested by the aforementioned test methods. The results were that 0.3% of the total hydrolysate consisted of fractions having a molecular weight of 5,000 to 10,000 daltons, the residual antigenic activity was no more than $10^{-6}$, the ratio at which lysine was freed was 14%, the free amino acid content was 11%, the ammonia content was 0.07%, the transmittance of a 10% solution was 98%, 5% solutions with unadjusted pH and a pH of 4 were stable when heated for 10 minutes at 120° C., and the antioxidant activity was the same as that of α-tocopherol. Tests by the aforementioned test methods revealed the following amino acid composition (per gram whey protein hydrolysate).

| | |
|---|---|
| L-alanine | 52.8 (mg) |
| L-arginine | 23.4 |
| L-aspartic acid (including L-asparagine) | 102.6 |
| L-cysteine | 17.1 |
| L-glutamic acid (including L-glutamine) | 185.1 |
| L-glycine | 18.8 |
| L-histidine | 17.7 |
| L-isoleucine | 59.9 |
| L-leucine | 100.1 |
| L-lysine | 94.6 |
| L-methionine | 15.8 |
| L-phenylalanine | 29.5 |
| L-proline | 61.4 |
| L-serine | 49.2 |
| L-threonine | 70.3 |
| L-tryptophan | 16.7 |
| L-tyrosine | 26.1 |
| L-valine | 54.7 |

EXAMPLE 2

1 kg of whey protein powder with a purity of 85% (by Denmark Protein) was dissolved in 19 kg of deionized water, the pH was adjusted to 10, 110,000 PUN units (130 PUN units per gram whey protein) of commercially available trypsin (by Novo Nordisk), 1,800,000 PUN units (2100 PUN units per gram whey protein) of Protease N Amano (by Amano Seiyaku), and 51,000 active units (60 active units per gram whey protein) of the product of ruptured *Lactobacillus bulgaricus* cells prepared by the same method as in Reference Example 1 above were added, the solution was hydrolyzed at 40° C., the content of free lysine was measured over time using a Biotech Analyzer (by Asahi Kasei Kogyo), the enzymes were inactivated by 2 seconds of heating at 130° C. when the free lysine content reached 17%, the product was cooled, the pH was then adjusted to 6.5 with citric acid, and the product was subjected to ultrafiltration with a 3,000 molecular weight fraction ultrafiltration membrane (Asahi Kasei Kogyo), concentrated, and spray dried to obtain about 800 g of a whey protein hydrolysate in the form of a powder.

The results obtained when the resulting whey protein hydrolysate was tested by the aforementioned test methods showed that 0.2% of the total hydrolysate consisted of fractions having a molecular weight of 5,000 to 10,000 daltons, the residual antigenic activity was no more than $10^{-6}$, the ratio at which lysine was freed was 17%, the free amino acid content was 13%, the ammonia content was 0.04%, the transmittance of a 10% solution was 99%, 5% solutions with unadjusted pH and a pH of 4 were stable when heated for 10 minutes at 120° C., and the antioxidant activity was the same as that of α-tocopherol.

EXAMPLE 3

1 kg of whey protein powder with a purity of 90% (by Biopol) was dissolved in 19 kg of deionized water and was sterilized for 15 seconds at 75° C., the pH was adjusted to 8.0, 100,000 PUN units (110 PUN units per gram whey protein) of commercially available papain (by Amano Seiyaku), 2,200,000 PUN units (2400 PUN units per gram whey protein) of Neutrase (by Novo Nordisk), and 90,000 active units (100 active units per gram whey protein) of the product of ruptured *Bifidobacterium breve* cells prepared by the same method as in Reference Example 1 above were added, the solution was hydrolyzed at 50° C., the content of free lysine was measured over time using a Biotech Analyzer (by Asahi Kasei Kogyo), the enzymes were inactivated by 15 minutes of heating at 85° C. when the free lysine content reached 20%, the product was cooled, the pH was then adjusted to 7.0 with citric acid, and the product was subjected to ultrafiltration with a 10,000 molecular weight fraction ultrafiltration membrane (by Nitto Denko), concentratio d, and spray dried to obtain about 800 g of a whey protein hydrolysate in the form of a powder.

The results obtained when the resulting whey protein hydrolysate was tested by the aforementioned test methods showed that 0.3% of the total hydrolysate consisted of fractions having a molecular weight of 5,000 to 10,000 daltons, the residual antigenic activity was no more than $10^{-6}$, the ratio at which lysine was freed was 20%, the free amino acid content was 15%, the ammonia content was 0.09%, the transmittance of a 10% solution was 98%, 5% solutions with unadjusted pH and a pH of 4 were stable when heated for 10 minutes at 120° C., and the antioxidant activity was the same as that of α-tocopherol.

EXAMPLE 4

1 kg of whey protein powder with a purity of 70% (by Mirai) was dissolved in 5.7 kg of deionized water, the pH was adjusted to 9.0, 1,600,000 PUN units (2000 PUN units per gram whey protein) of Bioplase (by Nagase Seikagaku Kogyo) and 63,000 active units (90 active units per gram whey protein) of the product of ruptured *Streptococcus lactis* cells prepared by the same method as in Reference Example 1 above were added, the solution was hydrolyzed at 45° C., the content of free lysine was measured over time using a Biotech Analyzer (by Asahi Kasei Kogyo), the enzymes were inactivated by 2 seconds of heating at 135° C. when the free lysine content reached 19%, the product was cooled, the pH was then adjusted to 7.0 with citric acid, and the product was subjected to ultrafiltration with a 10,000 molecular weight fraction ultrafiltration membrane (Asahi Kasei Kogyo) to obtain about 11 kg of a solution containing 8.4% whey protein hydrolysate.

The results obtained when the resulting whey protein hydrolysate was tested by the aforementioned test methods showed that 0.9% of the total hydrolysate consisted of fractions having a molecular weight of 5,000 to 10,000 daltons, the residual antigenic activity was no more than $10^{-6}$, the ratio at which lysine was freed was 19%, the free amino acid content was 14.5%, the ammonia content was 0.10%, the transmittance of a 10% solution was 98%, 5% solutions with unadjusted pH and a pH of 4 were stable when heated for 10 minutes at 120° C., and the antioxidant activity was the same as that of α-tocopherol.

EXAMPLE 5

1 kg of whey protein powder with a purity of 80% (by New Zealand Dairy Board) was dissolved in 12.3 kg of deionized water and sterilized for 15 seconds at 75° C., the pH was adjusted to 8.5, 80,000 PUN units (100 PUN units per gram whey protein) of commercially available papain (by Amano Seiyaku), 2,200,000 PUN units (2700 PUN units per gram whey protein) of Bioplase (by Nagase Seikagaku Kogyo), and 56,000 active units (70 active units per gram whey protein) of the product of ruptured *Streptococcus cremoris* cells prepared by the same method as in Reference Example 1 above were added, the solution was hydrolyzed at 45° C. as the pH was kept at 6.5, the content of free lysine was measured over time using a Biotech Analyzer (by Asahi Kasei Kogyo), the enzymes were inactivated by 5 minutes of heating at 90° C. when the free lysine content reached 17%, the product was cooled, the pH was then adjusted to 5.5 with citric acid, and the product was subjected to ultrafiltration with a 10,000 molecular weight fraction ultrafiltration membrane (by Nitto Denko), concentrated, and spray dried to obtain about 800 g of whey protein hydrolysate in the form of a powder.

The results obtained when the resulting whey protein hydrolysate was tested by the aforementioned test methods showed that 0.3% of the total hydrolysate consisted of fractions having a molecular weight of 5,000 to 10,000 daltons, the residual antigenic activity was no more than $10^{-6}$, the ratio at which lysine was freed was 17%, the free amino acid content was 13%, the ammonia content was 0.11%, the transmittance of a 10% solution was 99%, 5% solutions with unadjusted pH and a pH of 4 were stable when heated for 10 minutes at 120° C., and the antioxidant activity was the same as that of α-tocopherol.

EXAMPLE 6

1 kg of whey protein powder with a purity of 70% (California Protein) was dissolved in 7 kg of deionized water, the pH was adjusted to 8.0, 350,000 PUN units (500 PUN units per gram whey protein) of bromelain (by Amano Seiyaku), 2,300,000 PUN units (3300 PUN units per gram whey protein) of Neutrase (by Novo Nordisk), and 56,000 active units (80 active units per gram whey protein) of the product of ruptured *Lactobacillus bulgaricus* cells prepared by the same method as in Reference Example 1 above were added, the solution was hydrolyzed at 47° C., the content of free lysine was measured over time using a Biotech Analyzer (by Asahi Kasei Kogyo), the enzymes were inactivated by 15 minutes of heating at 85° C. when the free lysine content reached 17%, the product was cooled, the pH was then adjusted to 5.5 with citric acid, and the product was subjected to ultrafiltration with a 10,000 molecular weight fraction ultrafiltration membrane (by Nitto Denko), concentratio d, and spray dried to obtain about 800 g of whey protein hydrolysate in the form of a powder.

The results obtained when the resulting whey protein hydrolysate was tested by the aforementioned test methods showed that 0.4% of the total hydrolysate consisted of fractions having a molecular weight of 5,000 to 10,000 daltons, the residual antigenic activity was no more than $10^{-6}$, the ratio at which lysine was freed was 17%, the free amino acid content was 13%, the ammonia content was 0.10%, the transmittance of a 10% solution was 98%, and 5% solutions with unadjusted pH and a pH of 4 were stable when heated for 10 minutes at 120° C.

EXAMPLE 7

1 kg of whey protein powder with a purity of 80% (by Denmark Protein) was dissolved in 9 kg of deionized water, the pH was adjusted to 7.5, 1,600,000 PUN units (2000 PUN units per gram whey protein) of commercially available Neutrase (by Novo Nordisk) and 28,000 active units (35 active units per gram whey protein) of the product of ruptured *Bifidobacterium breve* cells prepared by the same method as in Reference Example 1 above were added, the solution was hydrolyzed at 45° C. as the pH was kept at 7.5, the content of free lysine was measured over time using a Biotech Analyzer (by Asahi Kasei Kogyo), the enzymes were inactivated by 20 minutes of heating at 90° C. when the free lysine content reached 12%, the product was cooled, the pH was then adjusted to 7.0 with citric acid, and the product was subjected to ultrafiltration with a 3,000 molecular weight fraction ultrafiltration membrane (by Asahi kasei Kogyo), concentrated, and spray dried to obtain about 800 g of whey protein hydrolysate in the form of a powder.

The results obtained when the resulting whey protein hydrolysate was tested by the aforementioned test methods showed that 0.4% of the total hydrolysate consisted of fractions having a molecular weight of 5,000 to 10,000 daltons, the residual antigenic activity was no more than $10^{-6}$, the ratio at which lysine was freed was 12%, the free amino acid content was 10%, the ammonia content was 0.09%, the transmittance of a 10% solution was 100%, and 5% solutions with unadjusted pH and a pH of 4 were stable when heated for 10 minutes at 120° C.

EXAMPLE 8

1 kg of commercially available whey protein powder with a whey protein content of 75% (by California Protein) was dissolved in 9 kg deionized water and sterilized for 5 minutes at 70° C., the pH was adjusted to 9.0, 1,500,000 PUN units (2000 PUN units per gram whey protein) of commercially available Protease N Amano (by Amano Seiyaku) and 40,000 active units (60 active units per gram whey protein) of the product of ruptured *Lactobacillus helveticus* cells prepared by the same method as in Reference Example 3 above were added, hydrolysis was begun at 50° C., the content of free lysine was measured briefly and over time using a Biotech Analyzer (by Asahi Kasei Kogyo), the zymolysis was stopped by inactivating the enzymes with 6 minutes of heating at 80° C. when the free lysine content reached 14%, and the product was lyophilized by a common method to obtain about 950 g of a peptide mixture from the whey protein.

The aforementioned manufacturing method was repeated twice, and the resulting peptide mixture was tested by the aforementioned test methods, with virtually no difference in the content of free amino acids or the total amount of free amino acids.

EXAMPLE 9

1 kg of commercially available wheat protein powder with a protein content of 80% (by Riken Vitamin: Emasoft EX-100) was dissolved in 9 kg deionized water, the pH was adjusted to 7.0, and the solution was sterilized for 5 minutes at 70° C. 2,000,000 PUN units (2500 PUN units per gram wheat protein) of commercially available pancreatin (by Amano Seiyaku) and 60,000 active units (75 active units per gram wheat protein) of the product of ruptured *Lactobacillus helveticus* cells prepared by the same method as in Reference Example 3 above were added to the wheat protein solution, hydrolysis was begun at 50° C., the content of free lysine was measured briefly and over time using a Biotech Analyzer (by Asahi Kasei Kogyo), the zymolysis was stopped by inactivating the enzymes with 10 minutes of heating at 80° C. when the free lysine content reached 34%, and the product was then lyophilized to obtain about 950 g of a peptide mixture from the wheat protein.

The aforementioned manufacturing method was repeated twice, and the resulting peptide mixture was tested by the aforementioned test methods, with virtually no difference in the content of free amino acids or the total amount of free amino acids.

EXAMPLE 10

500 g of commercially available wheat protein powder with a protein content of 80% (by Riken Vitamin: Emasoft EX-100) and 500 g of commercially available soybean protein powder with a protein content of 90% (by Fuji Seiyu: tradename SUPRO) were dissolved in 9 kg deionized water, the pH was adjusted to 7.0, and the solution was sterilized for 5 minutes at 70° C. 850,000 PUN units (1000 PUN units per gram protein) of commercially available pancreatin (by Amano Seiyaku), 1,700,000 PUN units (2000 PUN units per gram protein) of Protease N Amano (Amano Seiyaku), and 40,000 active units (47 active units per gram protein) of the product of ruptured *Lactobacillus helveticus* cells prepared by the same method as in Reference Example 3 above were added to the mixed protein solution, hydrolysis was begun at 50° C., the content of free lysine was measured briefly and over time using an HPLC (by Shimadzu Seisakusho), the zymolysis was stopped by inactivating the enzymes with 10 minutes of heating at 80° C. when the free lysine content reached 21%, and the product was then lyophilized to obtain about 950 g of a peptide mixture.

The aforementioned manufacturing method was repeated twice, and the resulting peptide mixture was tested by the aforementioned test methods, with virtually no difference in the content of free amino acids or the total amount of free amino acids.

EXAMPLE 11

500 g of commercially available whey protein powder with a whey protein content of 80% (by California Protein) and 500 g of commercially available soybean protein powder with a protein content of 90% (by Fuji Seiyu: tradename SUPRO) were dissolved in 9 kg deionized water and sterilized for 5 minutes at 70° C. the pH was adjusted to 9.0, 2,500,000 PUN units (4848 PUN units per gram protein) of commercially available Protease N Amano (by Amano Seiyaku) and 40,000 active units (48 active units per gram protein) of the product of ruptured *Lactobacillus helveticus* cells prepared by the same method as in Reference Example 3 above were added, hydrolysis was begun at 50° C., the content of free lysine was measured briefly and over time using a Biotech Analyzer (by Asahi Kasei Kogyo), the zymolysis was stopped by inactivating the enzymes with 6 minutes of heating at 80° C. when the free lysine content reached 18%, and the product was then lyophilized to obtain about 950 g of a peptide mixture.

The aforementioned manufacturing method was repeated twice, and the resulting peptide mixture was tested by the aforementioned test methods, with virtually no difference in the content of free amino acids or the total amount of free amino acids.

EXAMPLE 12

100 g of commercially available whey protein concentratio (Lacprodan 80: by Denmark Protein; 75% protein content) was dissolved in deionized water to a concentration of 10% and sterilized for 30 minutes at 65° C., the pH was adjusted to 8.5 with sodium hydroxide at 45° C., 150,000 PUN units (2000 PUN units per gram whey protein) of Pancreatin F (by Amano Seiyaku), 150,000 PUN units (2000 PUN units per gram whey protein) of commercially available Protease N Amano (by Amano Seiyaku), units (5000 PUN units per gram whey protein) of Actinase AS (by Kaken Pharma), 800 active units (10.7 active units per gram whey protein) of Protease A Amano (by Amano Seiyaku) were added, hydrolysis was begun, the content of free Phe in the hydrolysate was measured briefly and over time using an enzyme membrane sensor (Biotech Analyzer by Asahi Kasei Kogyo), the zymolysis was stopped by inactivating the enzymes with 10 minutes of heating at 85° C. when the free Phe content reached 90%, the precipitate was removed by celite filtration, and the product was lyophilized by a common method to obtain about 73 g of a peptide mixture.

5 g of the resulting lyophilized material was dissolved to a concentration of 10% in water, allowed to flow through a 5 cm (15 cm column packed with Sephadex G-10 (by Pharmacia), and eluted using deionized water to recover a peptide mixture with a low phenylalanine content. The eluate was lyophilized to obtain about 2.2 g of a peptide mixture with a low phenylalanine content.

The aforementioned manufacturing method was repeated three times, and the resulting peptide mixture with a low phenylalanine content was tested by the aforementioned tested methods, resulting in a Phe content of 0.2% per total amino acids, with virtually no difference in the Phe content of the three manufactured products.

EXAMPLE 13

200 g of commercially available bovine milk casein (ALACID: by New Zealand Dairy Board; 90% protein content) was suspended in deionized water, the pH was adjusted to 8.0 with 10% sodium hydroxide, the concentration was adjusted to 12% with deionized water, the solution was sterilized for 5 minutes at 90° C. and was then maintained at 50° C., 720,000 PUN units (4000 PUN units per gram casein protein) of Pancreatin F (by Amano Seiyaku) was added, hydrolysis was begun, five hours later, 900,000 units (5000 PUN units per gram casein protein) of Actinase AS (by Kaken Pharma) was added, the hydrolysis was continued, the content of free Phe in the hydrolysate was measured briefly and over time using an HPLC (by Shimadzu Seisakusho), the zymolysis was stopped by inactivating the enzymes with 10 minutes of heating at 85° C. when the free Phe content reached 90%, the precipitate was removed by ultrafiltration membrane (fraction molecular weight of 3000 daltons; Asahi Kasei Kogyo), and the product was lyophilized by a common method to obtain about 165 g of a peptide mixture.

150 g of the resulting lyophilized material was dissolved to a concentration of 20% in water, 35 g of activated carbon powder (Sirasagi (by Takeda Yakuhinn Kogyo)) was introduced, the material was allowed to stand for 15 hours at 4° C. and was then filtered to remove the activated carbon, the filtrate was allowed to flow at a flow ratio of 5 mL/min through a column packed with 190 mL adsorptive resin (KS-35, by Hokuetsu Tanso Kogyo), and the eluate was lyophilized to obtain about 112 g peptide mixture with a low phenylalanine content.

The aforementioned manufacturing method was repeated three times, and the resulting peptide mixture with a low phenylalanine content was tested by the aforementioned tested methods, resulting in a Phe content of 0.3% per total amino acids, with virtually no difference in the Phe content of the three manufactured products.

EXAMPLE 14

500 g of commercially available whey protein concentratio (Lacprodan 80, by Denmark Protein; 75% protein content) and 500 g of commercially available soybean protein powder (SUPRO, by Fuji Seiyu; 90% protein content) were dissolved to a concentration of 10% in deionized water and sterilized for 5 minutes at 70° C., the pH was adjusted to 9 with potassium hydroxide at 55° C., 1,237,500 PUN units (1500 PUN units per gram protein) of Pancreatin F (by Amano Seiyaku), 1,650,000 PUN units (2000 PUN units per gram protein) of Papain W-40 (by Amano Seiyaku), 3,300,000 PUN units (4000 PUN units per gram protein) of Actinase AS (by Kaken Pharma), and 16,500 active units (20 active units per gram protein) of Protease A Amano (by Amano Seiyaku) were added to begin hydrolysis, the content of free Phe in the hydrolysate was measured briefly and over time using an Enzyme membrane sensor (Biotech Analyzer (by Asahi Kasei Kogyo)), the enzymes were inactivated with 10 minutes of heating at 90° C. when the free Phe content reached 88%, the precipitate was removed by celite filtration, and the product was lyophilized by a common method to obtain about 720 g of a peptide mixture. 100 g of the resulting lyophilized material was dissolved to a concentration of 10% in water, the material was allowed to flow through a 37 cm×15 cm column packed with Cellulofine GCL-25 (by Seikagaku Kogyo) and was eluted using deionized water to recover a peptide mixture with a low phenylalanine content, which was lyophilized to obtain about 52 g of a peptide mixture with a low phenylalanine content.

The aforementioned manufacturing method was repeated three times, and the resulting peptide mixture with a low phenylalanine content was tested by the aforementioned tested methods, resulting in a Phe content of 0.4% per total amino acids, with virtually no difference in the Phe content of the three manufactured products.

INDUSTRIAL APPLICABILITY

As described above, the first and second of the present inventions are a palatable whey protein hydrolysate and a method for manufacturing the same. These inventions afford the following merits.

1) The whey protein hydrolysate pertaining to the present invention has exceptional gastrointestinal absorption properties and a good amino acid balance, allowing it to be used as a source of protein for infants with undeveloped digestion or the elderly and ill suffering from reduced digestion
2) The whey protein hydrolysate pertaining to the present invention has low residual antigenic activity, allowing it to be used as a source of protein for patients suffering from allergies, and to prevent allergies in infants, pregnant women, and the ill suffering from reduced immune functions.
3) The whey protein hydrolysate pertaining to the present invention has antioxidant action, has high thermostability and transparency, and is palatable, allowing it to be used as a source of protein for human milk-fortifying compositions and oral/enteric nutrients.
4) The method pertaining to the present invention allows whey protein hydrolysates having a wide range of applications to be manufactured.

The third of the present inventions is a novel method for manufacturing a peptide mixture. This invention affords the following merits.

5) Peptide mixtures with virtually constant amounts of various free amino acids and total amounts of free amino acids can be obtained.
6) Target peptide mixtures can always be obtained consistently.
7) Peptide mixtures of consistent quality can be easily manufactured.

The fourth of the present inventions is a novel method for manufacturing a peptide mixture with a low phenylalanine content, which is suitable for ingestion by patients suffering from phenylketonuria. The method of the present invention allows a manufactured product of high quality and a consistently low phenylalanine content to be readily manufactured. The peptide mixture with a low phenylalanine content manufactured by the method of the present invention is free of the drawbacks of poor taste and osmotic pressure found in conventional manufactured products, and can thus be used as a protein source in foods for infants, adults, and pregnant women suffering from phenylketonuria.

We claim:

1. A method for producing a peptide mixture from whey protein, wherein said method for producing a peptide mixture is characterized in that one or more proteases is or are added to an aqueous solution of starting material proteins consisting of one or more whey proteins to start the hydrolysis of the starting material protein, the amount of a specific amino acid, which is lysine, phenylalanine, leucine, or arginine, freed in the hydrolysate as a result of the hydrolysis is measured over time, the amount of the specific free amino acid is calculated with respect to the total amount of the specific amino acid contained in the starting material protein, and the hydrolysis is terminated immediately when the calculated value falls within a specific predetermined range.

2. A method for producing a peptide mixture from whey protein, comprising:
   adding at least one protease to an aqueous solution of at least one whey protein to hydrolyze the whey protein,
   measuring the amount of a free amino acid selected from the group consisting of lysine, phenylalanine, leucine and arginine produced during the hydrolysis of the whey protein,
   calculating the amount of the free amino acid with respect to the total amount of the amino acid contained in the whey protein, and
   terminating the hydrolysis when the calculated amount of the free amino acid with respect to the total amount of the amino acid contained in the whey protein falls within a predetermined range.

3. The method of claim 1, wherein the free amino acid is lysine.

4. The method of claim 1, wherein the free amino is phenylalanine.

5. The method of claim 1, wherein the free amino is leucine.

6. The method of claim 1, wherein the free amino is arginine.

7. The method of claim 1, wherein the amount of free amino acids in the hydrolysate when the hydrolysis is terminated is 10 to 15% with respect to the total amount of amino acids in the hydrosylate.

8. The method of claim 1, wherein less than 1% by weight of the proteins or peptides in the hydrolysate have a molecular weight between 5,000 and 10,000 daltons.

9. The method of claim 1, wherein the amount of free amino acids in the hydrolysate is 10 to 15% with respect to the total amount of amino acids in the hydrosylate when the hydrolysis is terminated.

10. The method of claim 1, wherein the free amino acid is lysine.

11. The method of claim 1, wherein the free amino is phenylalanine.

12. The method of claim 1, wherein the free amino is leucine.

13. The method of claim 1, wherein the free amino is arginine.

* * * * *